(12) United States Patent
Higashi et al.

(10) Patent No.: US 11,426,295 B2
(45) Date of Patent: Aug. 30, 2022

(54) TUBULAR MEDICAL INSTRUMENT AND TRANSFER DEVICE FOR A TUBULAR MEDICAL INSTRUMENT

(71) Applicant: KANEKA CORPORATION, Osaka (JP)

(72) Inventors: Ryogo Higashi, Settsu (JP); Shizuo Ichimura, Settsu (JP); Sadao Bessho, Settsu (JP)

(73) Assignee: KANEKA CORPORATION, Osaka (JP)

( * ) Notice: Subject to any disclaimer, the term of this patent is extended or adjusted under 35 U.S.C. 154(b) by 156 days.

(21) Appl. No.: 16/628,921

(22) PCT Filed: Jul. 9, 2018

(86) PCT No.: PCT/JP2018/025937
§ 371 (c)(1),
(2) Date: Jan. 6, 2020

(87) PCT Pub. No.: WO2019/009433
PCT Pub. Date: Jan. 10, 2019

(65) Prior Publication Data
US 2020/0138612 A1 May 7, 2020

(30) Foreign Application Priority Data
Jul. 7, 2017 (JP) .............................. JP2017-134170

(51) Int. Cl.
*A61F 2/915* (2013.01)
*A61F 2/966* (2013.01)

(52) U.S. Cl.
CPC .............. *A61F 2/915* (2013.01); *A61F 2/966* (2013.01); *A61F 2002/91533* (2013.01);
(Continued)

(58) Field of Classification Search
CPC .. A61F 2/915; A61F 2/966; A61F 2/82; A61F 2/86; A61F 2/89; A61F 2210/008;
(Continued)

(56) References Cited

U.S. PATENT DOCUMENTS 6,514,261 B1  2/2003  Randall et al.
6,652,576 B1 * 11/2003  Stalker ................... A61F 2/915
                                                             606/198

(Continued)

FOREIGN PATENT DOCUMENTS

JP   2002-525168 A   6/2002
JP     2008-193 A   1/2008

OTHER PUBLICATIONS

International Search Report (PCT/ISA/210) issued in PCT/JP2018/025937, dated Oct. 2, 2018.

*Primary Examiner* — Suba Ganesan
(74) *Attorney, Agent, or Firm* — Birch, Stewart, Kolasch & Birch, LLP

(57) ABSTRACT

A tubular medical instrument which can be easily ejected from a transfer device and accurately placed in a case the tubular medical instrument is released from the transfer device and placed at an affected area is provided. A tubular medical instrument includes ends portions, and a central portion, wherein each of the end portions is a region including one axial end of the tubular medical instrument and having a length of 10% with respect to an axial length $L_1$ of the tubular medical instrument, the central portion is a region including an axial center of the tubular medical instrument and having a length of 10% with respect to the axial length L1 of the tubular medical instrument, and a ratio (difference V/difference W) is 3 or more.

11 Claims, 9 Drawing Sheets

(52) U.S. Cl.
 CPC ............ *A61F 2002/91541* (2013.01); *A61F 2210/008* (2013.01); *A61F 2250/0039* (2013.01)

(58) Field of Classification Search
 CPC ...... A61F 2210/0039; A61F 2250/0039; A61F 2002/9155; A61F 2002/91558; A61F 2002/91566
 See application file for complete search history.

(56) References Cited

U.S. PATENT DOCUMENTS

| | | | |
|---|---|---|---|
| 7,632,303 B1 * | 12/2009 | Stalker | A61F 2/95 623/1.2 |
| 10,561,509 B2 * | 2/2020 | Slazas | A61F 2/90 |
| 2001/0025195 A1 * | 9/2001 | Shaolian | A61F 2/856 623/1.13 |
| 2003/0144671 A1 | 7/2003 | Brooks et al. | |
| 2007/0032860 A1 | 2/2007 | Brooks et al. | |
| 2015/0025615 A1 | 1/2015 | Brooks et al. | |
| 2016/0101221 A1 * | 4/2016 | Flomenblit | A61F 2/91 623/1.18 |
| 2018/0221181 A1 * | 8/2018 | Fischer | A61F 2/915 |
| 2018/0311406 A1 * | 11/2018 | Francis | C22F 1/10 |

* cited by examiner

[Fig. 1]
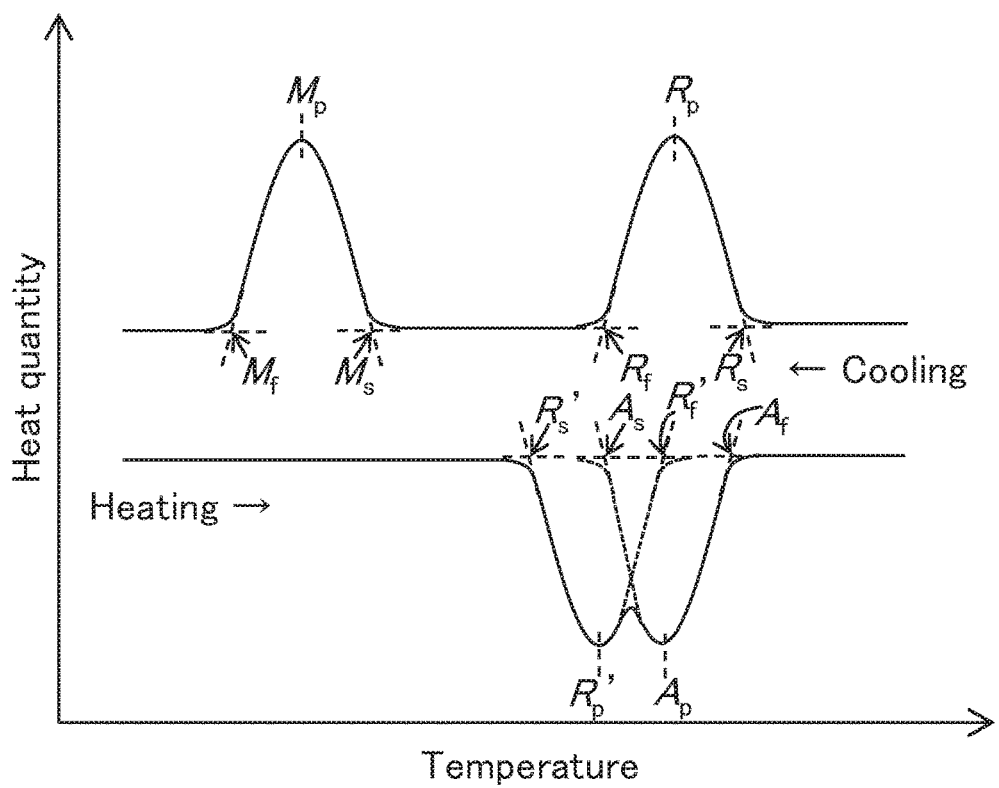
[Fig. 2]
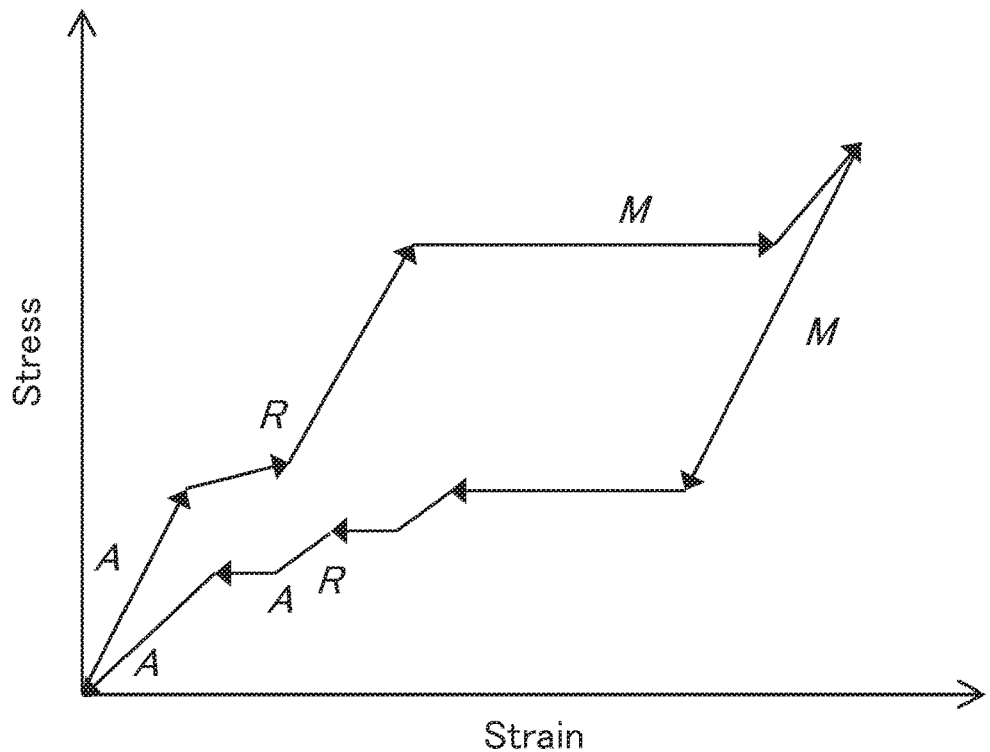

[Fig. 3]
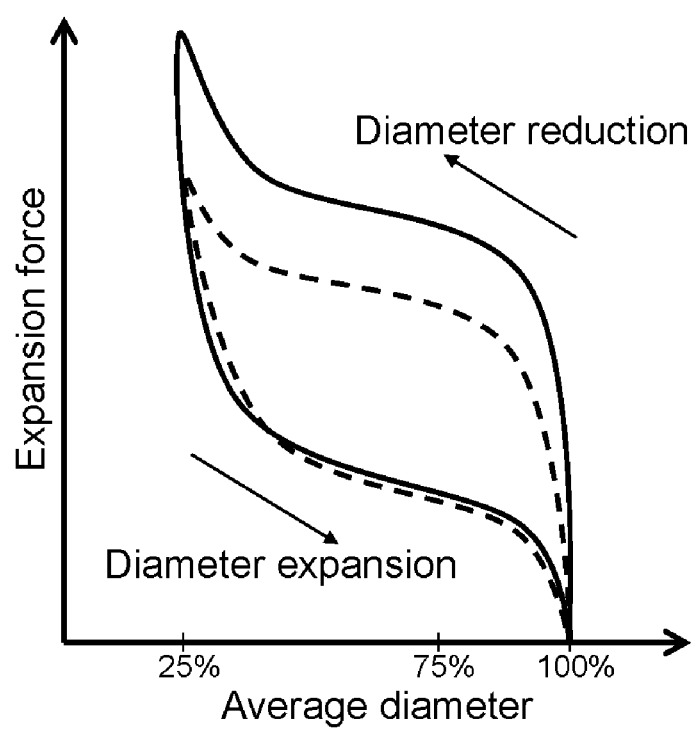

[Fig. 4]
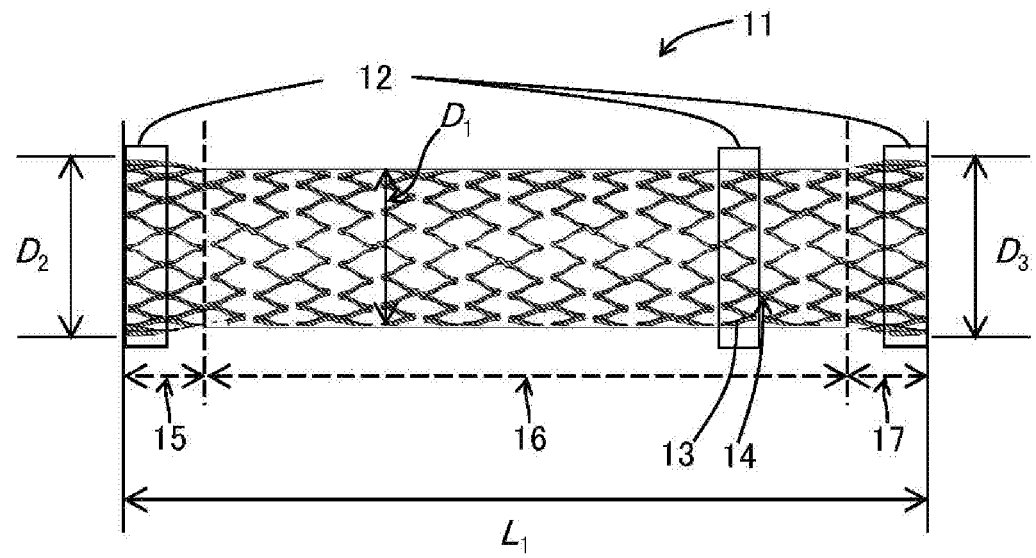
[Fig. 5]
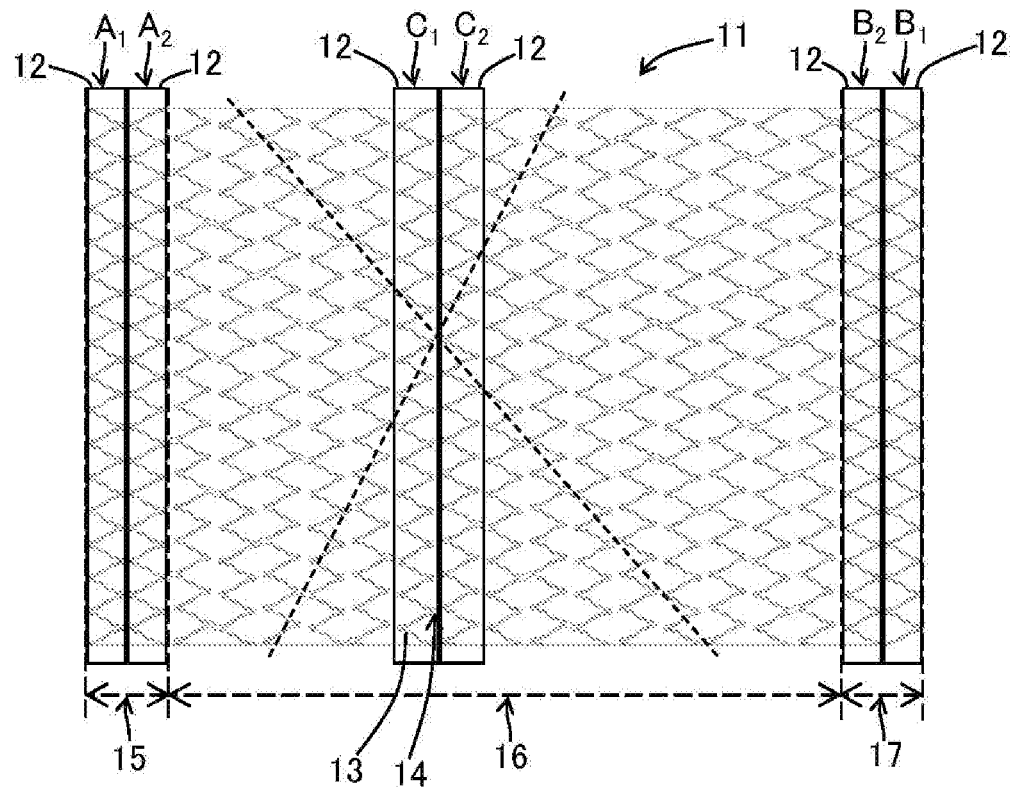

[Fig. 6]
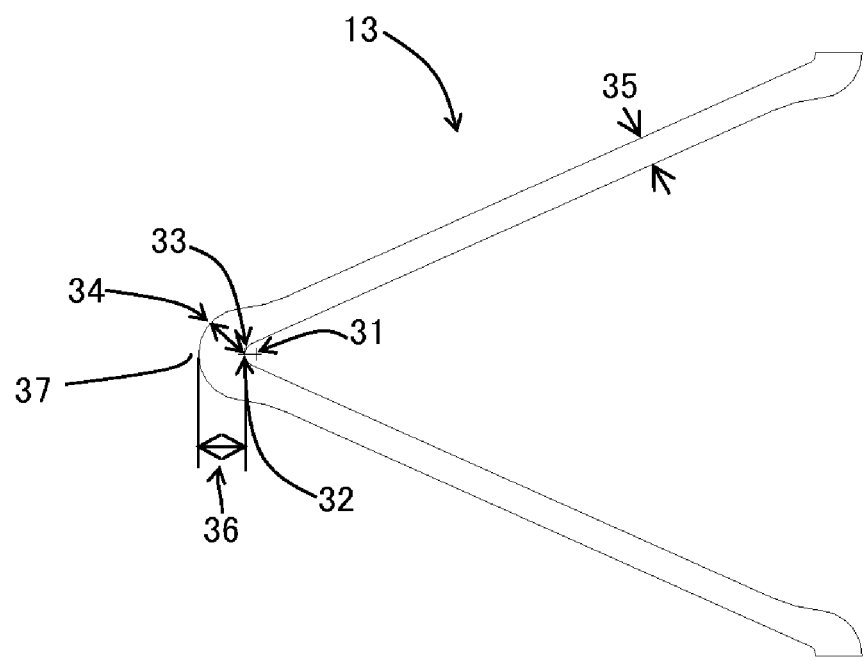
[Fig. 7]
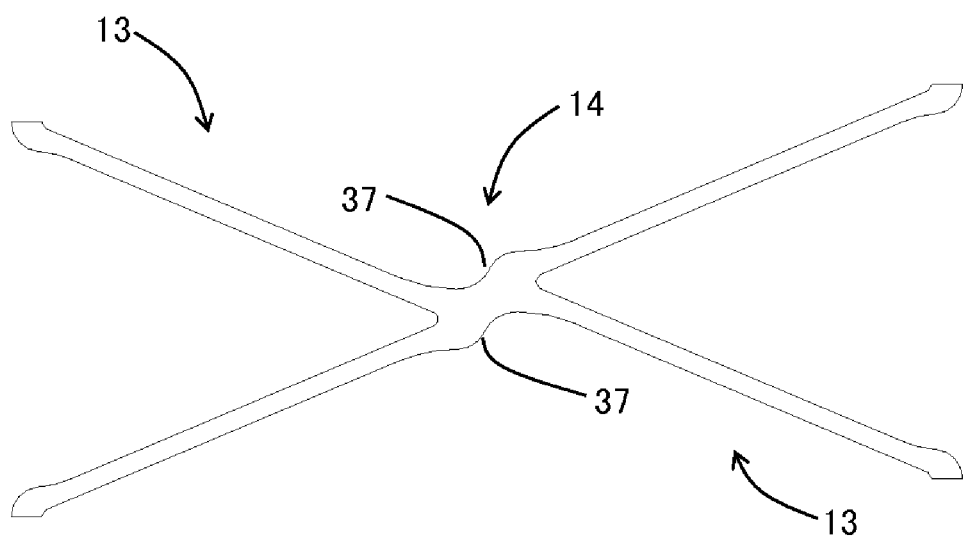

[Fig. 8]
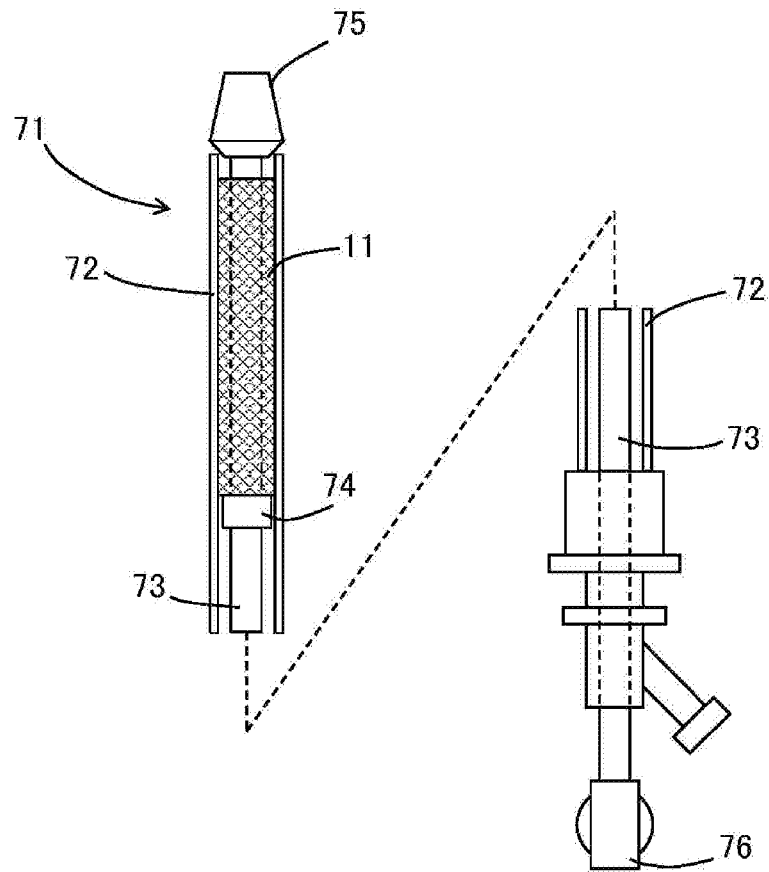
[Fig. 9]
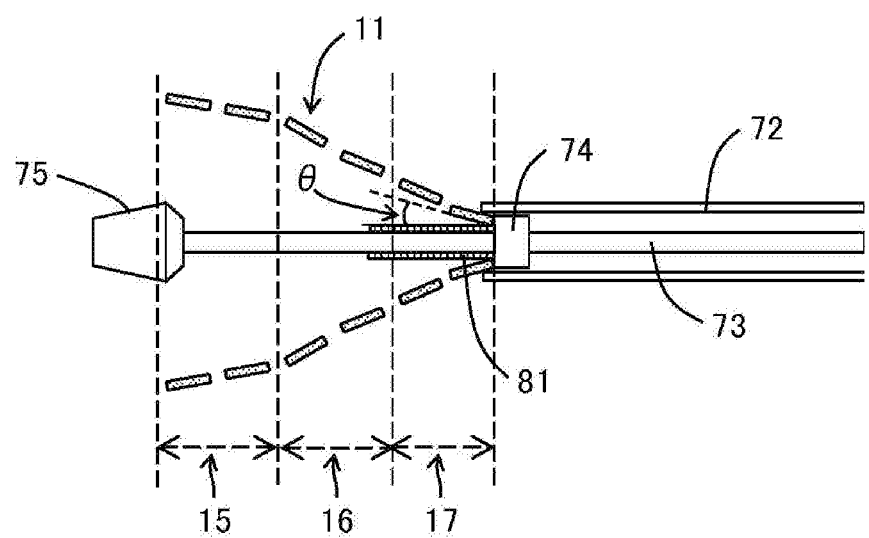

[Fig. 10]
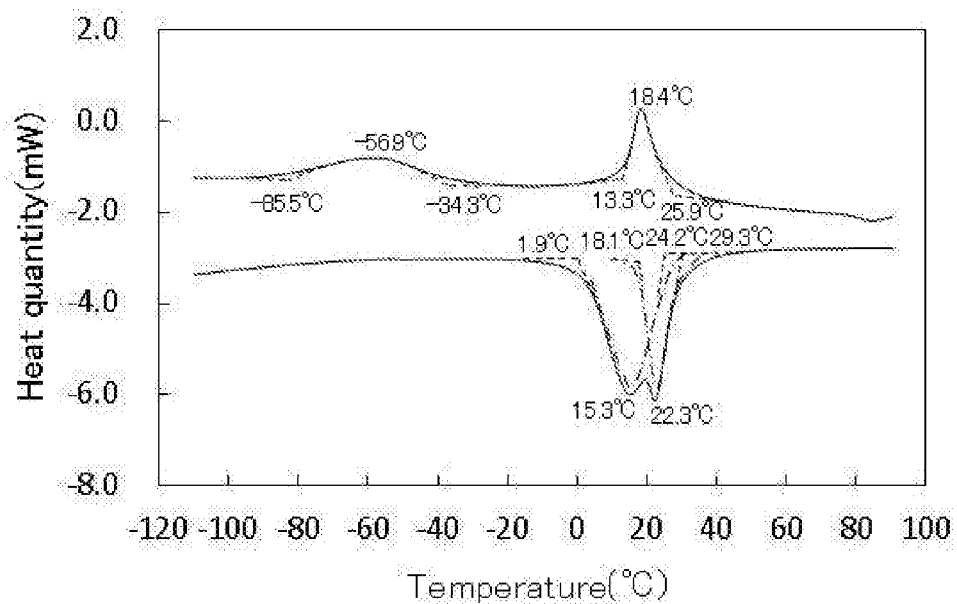
[Fig. 11]
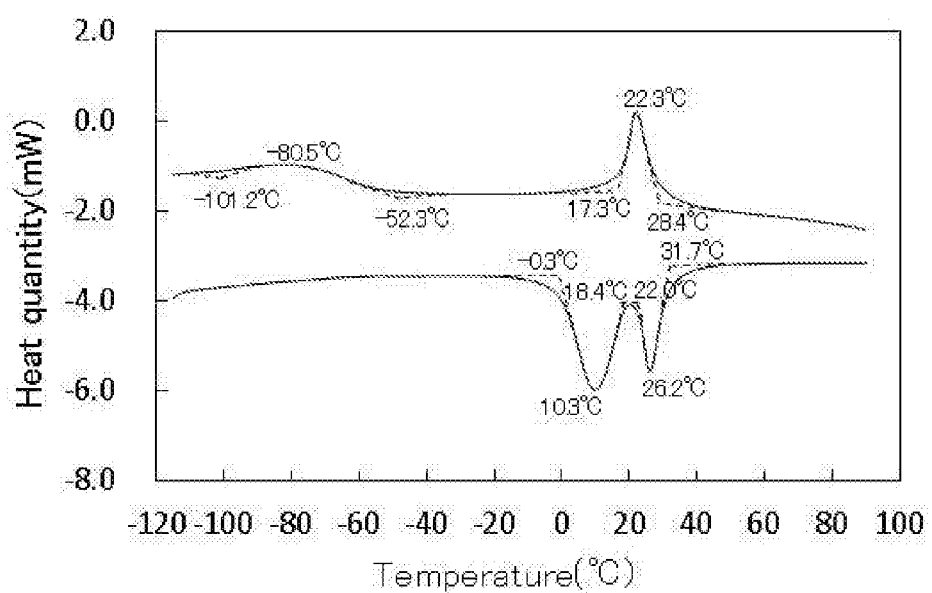

[Fig. 12]
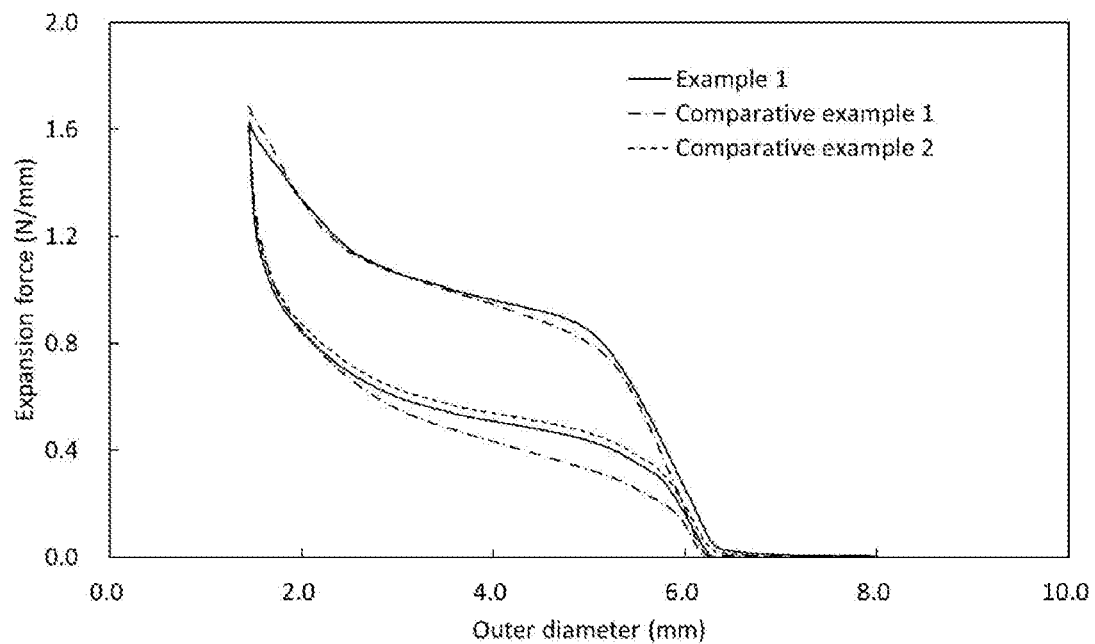
[Fig. 13]
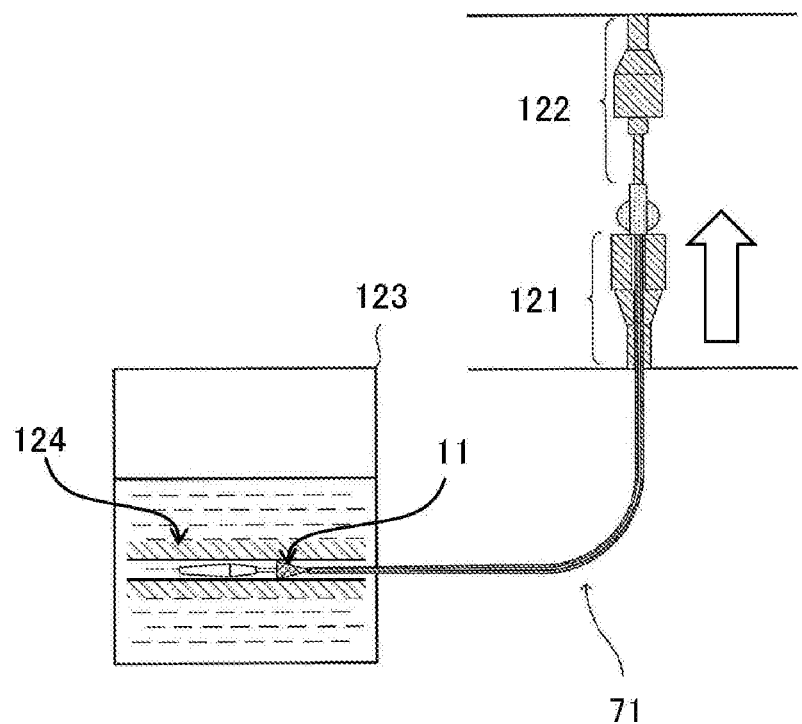

[Fig. 14]
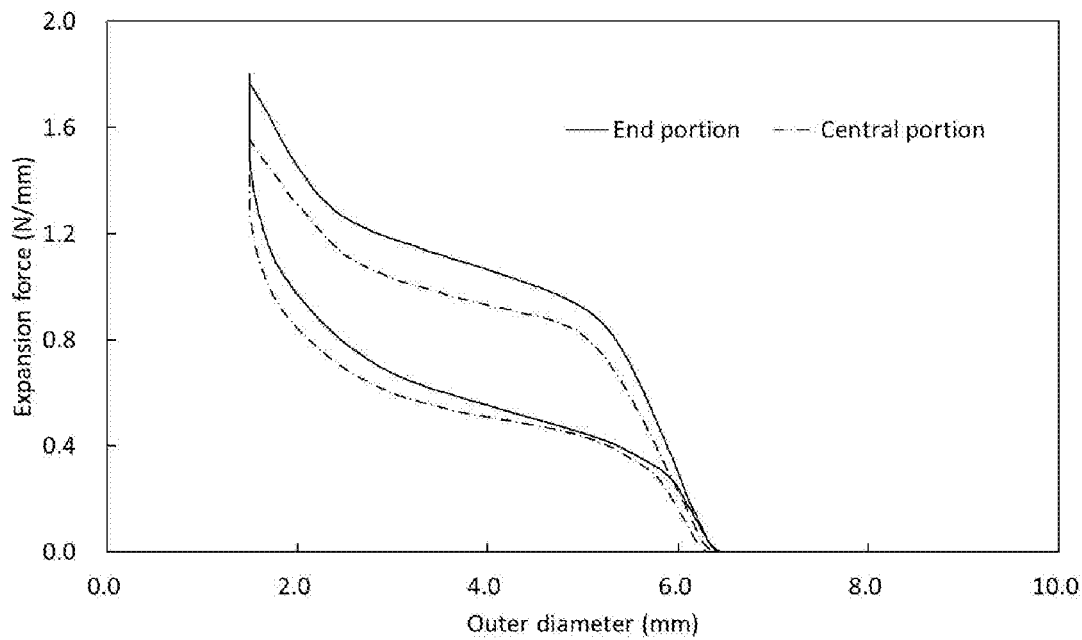
[Fig. 15]
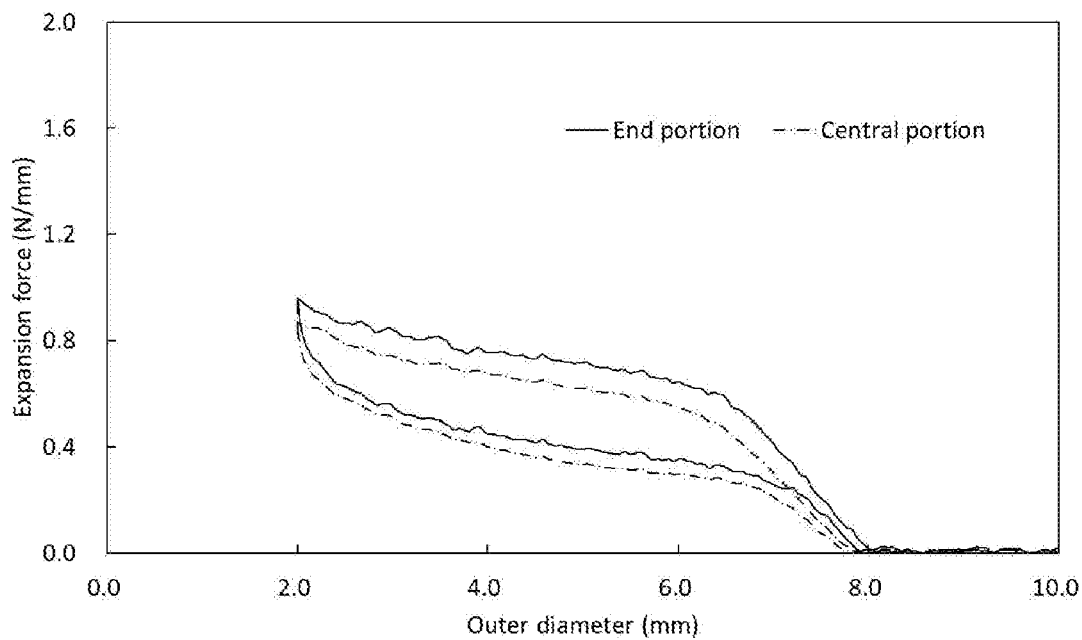

[Fig. 16]
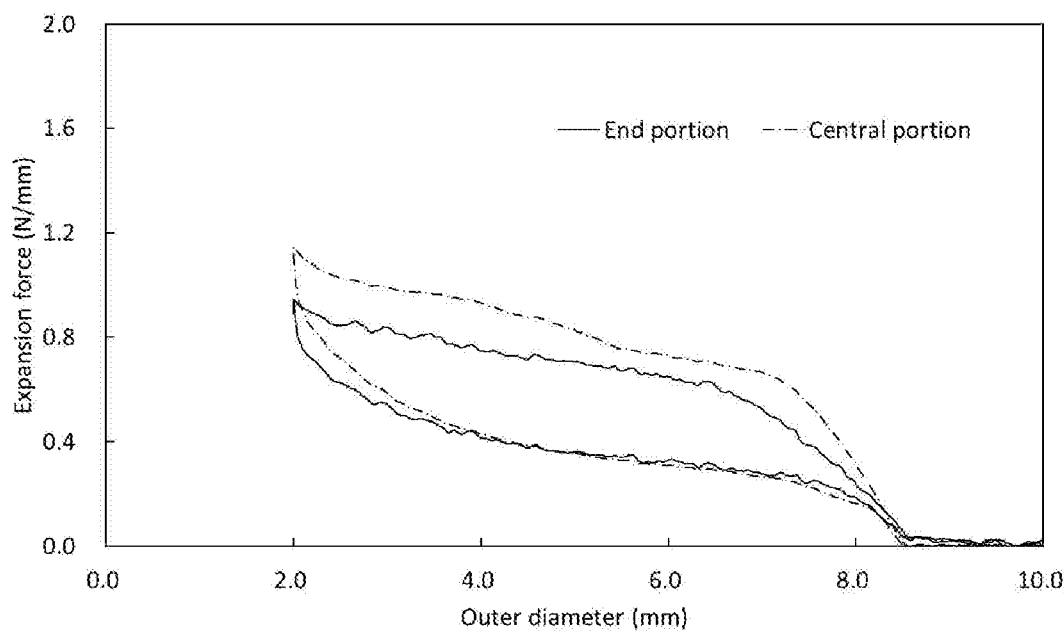
[Fig. 17]
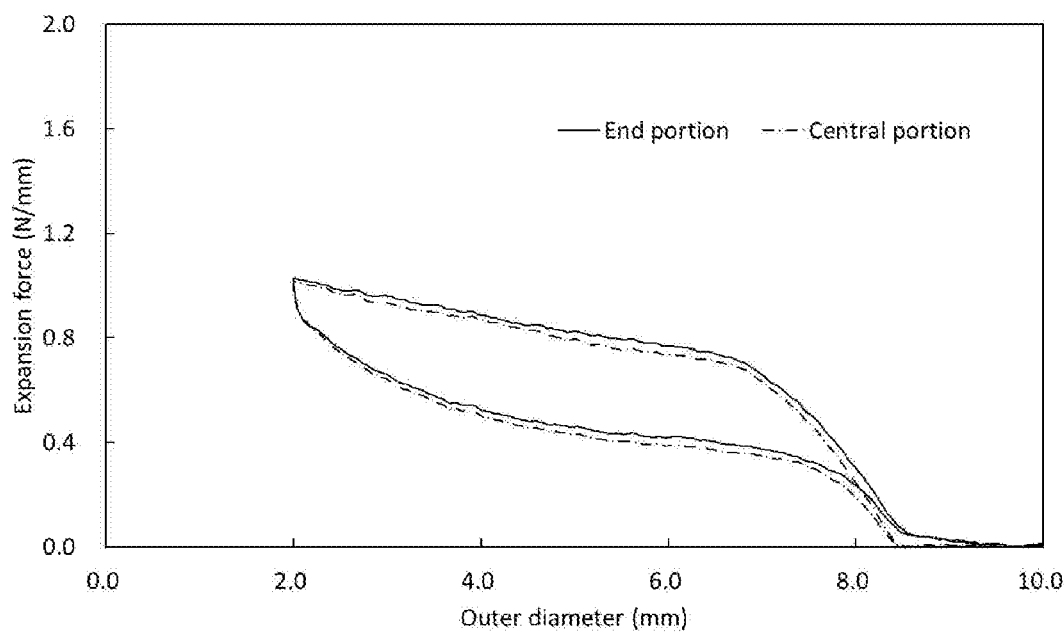

TUBULAR MEDICAL INSTRUMENT AND TRANSFER DEVICE FOR A TUBULAR MEDICAL INSTRUMENT

TECHNICAL FIELD

The present invention relates to a tubular medical instrument and a device for transferring a tubular medical instrument into a body.

BACKGROUND ART

In recent years, there has been developed a minimally invasive treatment technique that transfers and disposes a tubular medical instrument to and at an affected area in a body. As such a tubular medical instrument, for example, a stent, a stent graft, an obturator, an injection catheter, a prosthetic valve, or the like is used. Of these, a stent in general is a tubular medical instrument for treating various diseases caused by a stenosis or an occlusion of a blood vessel or other biological lumens. Specifically, using the tubular medical instrument, by disposing a stent at an affected area such as a stenosis site or an occlusion site, a lumen of the affected area can be radially expanded to keep the lumen diameter at a predetermined size. Stents are classified into a balloon expandable stent and a self-expanding stent. The balloon expandable stent is expanded to a predetermined size by a balloon mounted with a stent, and the self-expanding stent expands itself to a predetermined size by removing an external member that restricts the expansion of the stent.

The minimally invasive treatment technique uses a transfer device which transfers the tubular medical instrument to an affected area through a body lumen, and places the tubular medical instrument at the affected area. The transfer device includes a tube and transfers the tubular medical instrument to the affected area through a body lumen in a state where the tubular medical instrument is held in the tube lumen. In general, a tubular medical instrument is loaded in a state of being reduced in diameter to a lumen inner diameter of the transfer device or less. To load the tubular medical instrument into the lumen of the transfer device, a method is generally employed, in which the tubular medical instrument is reduced in diameter to the lumen inner diameter of the transfer device or less, and then an end portion of the tubular medical instrument is pushed so as to load the tubular medical instrument into the lumen of the transfer device. After the tubular medical instrument is transferred to the affected area, the tubular medical instrument can be placed at the affected area by releasing the tubular medical instrument from the inside of the lumen of the transfer device. In order to release the tubular medical instrument from the lumen of the transfer device, the transfer device is provided with a mechanism that pushes the end portion of the tubular medical instrument out of the lumen.

When the tubular medical instrument with an increased expansion force is released from the lumen of the transfer device, the end portion of the tubular medical instrument is rapidly expanded. For this reason, there has been a case where the expansion force acts as a driving force and causes the tubular medical instrument to be placed by jumping over the affected area. Such a phenomenon is called a jumping phenomenon, and in a case the jumping phenomenon occurs, the tubular medical instrument cannot be placed at the affected area, and treatment cannot be performed. For this reason, treatment needs to be performed again, which increases the burden on a patient.

For example, Patent Documents 1 and 2 are known as techniques for suppressing the occurrence of the jumping phenomenon. Of these, Patent Document 1 describes a self-expanding stent including a stent main body and a stent end portion continuously provided at one end of the stent main body. An expansion force of the stent end portion is 0.05 to 0.84 N/cm, and an expansion force of the stent main body is 1.2 to 3.0 times that of the end portion. Patent Document 2 describes a device for introducing a stent into a body blood vessel. The device includes an elongated housing for providing a passage in the inside, a movable member disposed in the passage, actuating means connected to the housing so as to be able to move the movable member in a first direction in an incremental manner, a catheter connected to the movable member, an inner tube extending through the catheter, a tip attached to the inner tube, and a stabilization element extending through the catheter to maintain a position of a stent during withdrawal of the catheter.

RELATED ART DOCUMENTS

Patent Documents

Patent Document 1: JP-A-2008-193
Patent Document 2: JP-A-2002-525168

DISCLOSURE OF THE INVENTION

Problems to be Solved by the Invention

The stent described in Patent Document 1 reduces the expansion force in both end portions of the stent as compared to a central portion of the stent. For this reason, there has been a case where, in a case the stent is disposed at an affected area such as a stenosis site or an occlusion site, the stent end portion cannot sufficiently expand a body lumen of the affected area due to the expansion force shortage. Therefore, with this stent, there has been possibility that a restenosis occurs at the affected area.

In order to further develop minimally invasive treatment, it is important to further reduce the diameter of the tube for holding the tubular medical instrument provided in a transfer device for a tubular medical instrument, and to further improve the operability and pass ability of the transfer device for a tubular medical instrument.

However, the device described in Patent Document 2 is provided with the movable member in the passage inside the housing and also provided with the stabilization element for keeping the position of the stent, and has a structure in which these are controlled by an operation unit. For this reason, the structure of the catheter and the operation unit is complicated, and it is difficult to reduce the diameter of the catheter. Therefore, these techniques cannot further develop minimally invasive treatment.

Further, the tubular medical instrument is also required to have a large expansion force in a radial direction in order to maintain a lumen diameter while expanding a body lumen of an affected area.

In view of the above, with respect to a technique for suppressing the occurrence of the jumping phenomenon when the tubular medical instrument is released from the inside of the lumen of the transfer device described in Patent Documents 1 and 2, the present inventors have examined the degree of suppression of the jumping phenomenon when the tubular medical instrument is released from the transfer device in a case where the tubular medical instrument having a large expansion force in a radial direction is reduced in diameter and loaded into the transfer device. As a result, it has been found that the degree of suppression of the jumping phenomenon in the techniques of Patent Documents 1 and 2 is not sufficient.

The present invention has been made focusing on the above circumstances, and an object of the present invention is to provide a tubular medical instrument which can be easily ejected from a transfer device to be released from the inside of a lumen of the transfer device and accurately placed at an affected area, and a transfer device for a tubular medical instrument having the tubular medical instrument.

Solutions to the Problems

The tubular medical instrument of the present invention which is able to solve the above problem made of an alloy comprises one end portion, the other end portion, and a central portion, wherein the one end portion is a region including one axial end of the tubular medical instrument and having a length of 10% with respect to an axial length $L_1$ of the tubular medical instrument, the other end portion is a region including the other axial end of the tubular medical instrument and having a length of 10% with respect to the axial length $L_1$ of the tubular medical instrument, the central portion is a region including an axial center of the tubular medical instrument and having a length of 10% with respect to the axial length $L_1$ of the tubular medical instrument, and a ratio (difference V/difference W) calculated by the following test method is 3 or more: the tubular medical instrument is subjected to a contraction-expansion cycle where the tubular medical instrument is contracted from an expanded state to a contracted state such that an average diameter of the tubular instrument becomes 25%, and then allowed to expand from the contracted state to the expanded state, wherein the difference V is a difference between an expansion force per unit length in the radial direction in the central portion and an expansion force per unit length in the radial direction in the one end portion or the other end portion, whichever is smaller, at the time when the average diameter becomes 75% as the tubular medical instrument is being contracted from the expanded state such that the average diameter of the tubular instrument becomes 25%, and the difference W is a difference between an expansion force per unit length in the radial direction in the central portion and an expansion force per unit in the radial direction in the one end portion or the other end portion, whichever is smaller, at the time when the average diameter becomes 75% as the tubular medical instrument is being allowed to expanded from the contracted state.

The above problem is also able to solve by a tubular medical instrument made of an alloy comprises one end portion, the other end portion, and a central portion, wherein the one end portion is a region including one axial end of the tubular medical instrument and having a length of 10% with respect to an axial length $L_1$ of the tubular medical instrument, the other end portion is a region including the other axial end of the tubular medical instrument and having a length of 10% with respect to the axial length $L_1$ of the tubular medical instrument, and the central portion is a region including an axial center of the tubular medical instrument and having a length of 10% with respect to the axial length $L_1$ of the tubular medical instrument, wherein, when the tubular medical instrument in the expanded state is contracted such that the average diameter of the tubular instrument becomes 75%, an expansion force per unit length in a radial direction in the one end portion and in the other end portion is larger than an expansion force per unit length in the radial direction in the central portion, wherein the alloy at the one end portion or the other end portion has an austenitic phase transformation finish temperature $A_f$ of a body temperature or less, and a difference X between an R'-phase transformation finish temperature $R_f'$ and the austenitic phase transformation finish temperature $A_f$ of 1° C. or more and 12° C. or less, and wherein the alloy at the central portion has the austenitic phase transformation finish temperature $A_f$ of a body temperature or less, and a difference Y between the R'-phase transformation finish temperature $R_f'$ and the austenitic phase transformation finish temperature $A_f$ of larger than the difference X.

A maximum outer diameter $D_2$ of the one end portion and a maximum outer diameter $D_3$ of the other end portion are preferred larger than a maximum outer diameter $D_1$ of the central portion.

The tubular medical instrument comprises annular sections comprising a wavy constituent, wherein the annular sections are formed to include the wavy constituent and aligned in an axial direction, the wavy constituent is expandable in a circumferential direction, at least part of the wavy constituent constituting one of the annular sections is connected to at least part of a wavy constituent constituting another adjacent annular section at their vertices, and a number a or a number b, whichever is smaller, is preferred larger than a number c, where the number a is defined as a number of connecting portions between an annular section $A_1$ in the one end portion and another annular section $A_2$ adjacent to the annular section $A_1$, the number b is defined as a number of connecting portions between an annular section $B_1$ in the other end portion and another annular section $B_2$ adjacent to the annular section $B_1$, and the number c is defined as a number of connecting portions between an annular section $C_1$ in the central portion and another annular section $C_2$ adjacent to the annular section $C_1$.

The tubular medical instrument comprises annular sections, a first annular section of said annular sections at one end of the tubular medical instrument is connected at all vertices to another annular section adjacent to the first annular section, a second annular section of said annular sections at another end of the tubular medical instrument is connected at all vertices to another annular section adjacent to the second annular section, and at least part of the third annular section of said annular sections in the central portion is connected at part of vertices to another annular section adjacent to the third annular section, and is not preferred connected at part of vertices.

The alloy preferably has the austenitic phase transformation finish temperature $A_f$ of 15° C. or more and 37° C. or less.

The alloy in the one end portion or the other end portion preferably has a difference between an R'-phase transformation peak temperature $R_p'$ and an austenitic phase transformation peak temperature $A_p$ of 1° C. or more and 12° C. or less.

The alloy in the one end portion or the other end portion preferably has a R'-phase transformation finish temperature $R_f'$ higher than an austenitic phase transformation start temperature $A_s$.

The alloy in the one end portion or the other end portion preferably has the R'-phase transformation finish temperature $R_f'$ higher than the austenitic phase transformation start temperature $A_s$ by 1° C. or more and 10° C. or less.

The tubular medical instrument is preferred a self-expanding stent.

The present invention also includes a transfer device for a tubular medical instrument including the above tubular medical instrument.

The transfer device for the tubular medical instrument comprise an outer shaft t having a lumen, the tubular medical instrument stored in the lumen of the outer shaft, an inner shaft disposed in the lumen of the tubular medical instrument, and a tubular member provided between the tubular medical instrument and the inner shaft and on an inner side of at least one of one end portion and the other end portion of the tubular medical instrument, wherein a difference between an inner diameter of the tubular medical instrument stored in the lumen of the outer shaft and an outer diameter of the tubular member is 0.05 mm or more and 0.35 mm or less.

Effects of the Invention

According to the present invention, an expansion force in a radial direction is appropriately adjusted in both end portions and a central portion in an axial direction of a tubular medical instrument or an expansion force in a radial direction is appropriately adjusted and an alloy the phase transformation temperature of which has a predetermined relationship is used as a material of the tubular medical instrument. For this reason, the tubular medical instrument can be easily ejected from a transfer device, and the tubular medical instrument released from the inside of the lumen of the transfer device can be accurately placed at an affected area.

BRIEF DESCRIPTION OF THE DRAWINGS

FIG. 1 is a graph showing a change in heat quantity in a case the nickel-titanium alloy exhibits a two-step phase transformation.

FIG. 2 is a graph showing a change in stress and strain in a case the nickel-titanium alloy exhibits a two-step phase transformation.

FIG. 3 is a schematic diagram showing a relationship between an average diameter of the tubular medical instrument and an expansion force per unit length in a radial direction.

FIG. 4 is a schematic view for describing a self-expanding stent as one form of the tubular medical instrument according to the present invention.

FIG. 5 is a developed view of the self-expanding stent shown in FIG. 4 in the expanded state.

FIG. 6 is a schematic view showing the wavy constituent constituting the self-expanding stent shown in FIG. 4.

FIG. 7 is a schematic view showing the connecting portion of adjacent two wavy constituents of the self-expanding stent shown in FIG. 4.

FIG. 8 is a general schematic view of a transfer device for a tubular medical instrument having the self-expanding stent.

FIG. 9 is a schematic view showing a state where the self-expanding stent is released from the transfer device.

FIG. 10 is a graph showing the results of measuring the heat quantity of the self-expanding stent used in the example.

FIG. 11 is a graph showing the results of measuring the heat quantity of the self-expanding stent used in the comparative example.

FIG. 12 is a graph showing the relationship between the outer diameter of the stent and the expansion force per unit length in the radial direction of the stent for the entire self-expanding stent.

FIG. 13 is a schematic diagram of an apparatus used to evaluate the placement accuracy of the tubular medical instrument in a case the tubular medical instrument loaded into a lumen of the transfer device is released from the lumen.

FIG. 14 is a graph showing the relationship between the outer diameter of the stent and the expansion force at the end portion and in the central portion of the stent.

FIG. 15 is a graph showing the relationship between the outer diameter of the stent and the expansion force at the end portion and in the central portion of the stent.

FIG. 16 is a graph showing the relationship between the outer diameter of the stent and the expansion force at the end portion and in the central portion of the stent.

FIG. 17 is a graph showing the relationship between the outer diameter of the stent and the expansion force at the end portion and in the central portion of the stent.

MODE FOR CARRYING OUT THE INVENTION

The present inventors have made diligent studies on a tubular medical instrument that can be easily ejected from a transfer device to be released from the inside of a lumen of the transfer device and accurately placed at an affected area. As a result, the present inventors have found that, by appropriately adjusting an expansion force in a radial direction in both end portions and a central portion in an axial direction of a tubular medical instrument or by appropriately adjusting an expansion force in a radial direction, and then using an alloy the phase transformation temperature of which has a predetermined relationship as a material of the tubular medical instrument, the tubular medical instrument can be easily ejected from a transfer device to be released from the inside of the lumen of the transfer device and can be accurately placed at an affected area, and have completed the present invention.

Hereinafter, the tubular medical instrument and the transfer device for a tubular medical instrument according to the present invention will be described in detail with reference to the drawings, however, the present invention is not limited to the drawings.

<Tubular Medical Instrument>

The tubular medical instrument according to the present invention is a tubular body, the shape of which is not particularly limited, but preferably cylindrical.

The tubular medical instrument is expandable in a radial direction from a first diameter to a second diameter. That is, the size of the tubular medical instrument of the present invention in a radial direction is variable. The first diameter is, for example, a diameter in a case a compressive force is applied in the radial direction of the tubular medical instrument and the diameter is reduced. The second diameter is, for example, a diameter in a case the compressive force that is applied in the radial direction of the tubular medical instrument is released and the diameter is expanded.

The tubular medical instrument is made from an alloy. A type of the alloy will be described in detail later.

Then, in the tubular medical instrument of the present invention, the tubular medical instrument comprises one end portion, the other end portion, and a central portion wherein the one end portion is a region including one axial end of the tubular medical instrument and having a length of 10% with respect to an axial length $L_1$ of the tubular medical instrument, the other end portion is a region including the other axial end of the tubular medical instrument and having a length of 10% with respect to the axial length $L_1$ of the tubular medical instrument, and the central portion is a region including an axial center of the tubular medical instrument and having a length of 10% with respect to the axial length $L_1$ of the tubular medical instrument, wherein, when the tubular medical instrument in the expanded state is contracted such that the average diameter of the tubular instrument becomes 75%, an expansion force per unit length in a radial direction in the one end portion and in the other end portion is larger than an expansion force per unit length in the radial direction in the central portion, wherein the alloy at the one end portion or the other end portion has an austenitic phase transformation finish temperature $A_f$ of a body temperature or less, and a difference X between an R'-phase transformation finish temperature $R_f'$ and the austenitic phase transformation finish temperature $A_f$ of 1° C. or more and 12° C. or less, and wherein the alloy at the central portion has the austenitic phase transformation finish temperature $A_f$ of a body temperature or less, and a difference Y between the R'-phase transformation finish temperature $R_f'$ and the austenitic phase transformation finish temperature $A_f$ of larger than the difference X.

The diameter is reduced such that the average diameter of the tubular medical instrument becomes 75%. In this case, a relatively larger expansion force per unit length in the radial direction in the one end portion and the other end portion than expansion force per unit length in the radial direction in the central portion makes the central portion well balanced with an appropriate expansion force and flexibility, which enables both end portions of the tubular medical instrument to be pushed and moved without buckling deformation of the transfer device. Further, by controlling the expansion force of the tubular medical instrument in this manner, it is possible to prevent the tubular medical instrument placed at an affected area from moving from the affected area, and also prevent restenosis in the tubular medical instrument. Furthermore, since the end portion of the tubular medical instrument is susceptible to contraction and deformation due to physical stress caused by being placed in a body lumen, a stent edge restenosis, which becomes a problem after the tubular medical instrument is placed in a body lumen, can be effectively suppressed by making the expansion force of the end portion relatively larger than the central portion of the tubular medical instrument.

The tubular medical instrument of the present invention satisfies the above-mentioned requirements in a case the expansion force in each region of 10% in length with respect to the axial length $L_1$ of the tubular medical instrument is compared, and a region including the one end portion or the other end portion has a larger expansion force than a region including the central portion and is a strong region. On the other hand, the region including the central portion has a smaller expansion force than the region including the one end portion or the other end portion, and is a weak region.

The strong region including the one end portion or the other end portion with respect to the entire tubular medical instrument may have a length exceeding 10% with respect to the axial length $L_1$ of the tubular medical instrument, and may be, for example, 11% or more, or 12% or more. Further, the length of the strong region is preferably 20% or less, more preferably 18% or less, and still more preferably 15% or less with respect to the axial length $L_1$ of the tubular medical instrument.

The weak region including the central portion with respect to the entire tubular medical instrument is the remaining region excluding the strong region. The length of the weak region is preferably 20% or more, more preferably 30% or more, with respect to the axial length $L_1$ of the tubular medical instrument. The weak region is preferably 80% or less, more preferably 70% or less, and still more preferably 60% or less.

The axial length $L_1$ of the tubular medical instrument is appropriately selected based on a length of an affected area to be treated. For example, the axial length $L_1$ of the self-expanding stent for treatment of a lower extremity artery is, for example, 20 to 200 mm.

In the tubular medical instrument, the expansion force per unit length in the radial direction at the time of diameter reduction from a diameter expansion state can be evaluated by a Radial Resistive Force (hereinafter sometimes referred to as RRF). The RRF is an expansion force against a compressive force that the tubular medical instrument receives from the radial direction.

The expansion force at the time of diameter reduction from the diameter expansion state per unit length in the radial direction at the one end portion and the other end portion is preferably 0.010 to 0.500 N/mm, more preferably 0.020 to 0.490 N/mm, and still more preferably 0.030 to 0.480 N/mm larger than the expansion force at the time of diameter reduction from the diameter expansion state per unit length in the radial direction at the central portion.

On the other hand, in the entire tubular medical instrument, the expansion force at the time of diameter reduction from the diameter expansion state is preferably, for example, 0.200 to 1.500 N/mm in order to appropriately expand a body lumen and maintain the expansion state. If the expansion force at the time of diameter reduction from the diameter expansion state in the entire tubular medical instrument is too small, it becomes difficult to expand the body lumen or maintain the expansion state due to the expansion force shortage. Further, if the expansion force at the time of diameter reduction from the diameter expansion state is insufficient, the tubular medical instrument may drop out from the placed position to move. The expansion force at the time of diameter reduction from the diameter expansion state in the entire tubular medical instrument is more preferably 0.400 N/mm or more, or still more preferably 0.800 N/mm or more. The expansion force at the time of diameter reduction from the diameter expansion state in the entire tubular medical instrument is preferably as large as possible from the viewpoint of expansion of a body lumen and maintenance of the expansion state. However, if the expansion force at the time of diameter reduction from the diameter expansion state in the entire tubular medical instrument is too large, the body lumen may be damaged. Therefore, the expansion force of the entire tubular medical instrument is preferably 1.500 N/mm or less, more preferably 1.200 N/mm or less, and still more preferably 1.100 N/mm or less.

The expansion force can be measured, for example, by a radial force measuring machine commercially available from Machine Solutions Inc. (hereinafter sometimes referred to as MSI), Blockwise Engineering LLC (hereinafter sometimes referred to as Blockwise), and the like.

The measurement of the expansion force can be carried out, for example, by measuring a diameter reduction load in a case a sample cut from each region of the one end portion, the other end portion, and the central portion, or the entire tubular medical instrument is compressed from the radial direction at a velocity of 0.1 mm/sec and reduced in diameter to a diameter of a value obtained by subtracting 2.5 mm from a maximum outer diameter $D_1$ at the central portion of the tubular medical instrument under an atmosphere of 37.0°

C.±2.0° C., and dividing the diameter reduction load by a length of each region or a length of the tubular medical instrument.

All regions of the one end portion, the central portion, and the other end portion may have the same or different outer diameter, or the one end portion and the other end portion may have the same outer diameter, which is different from the one in the region of the central portion. The diameter of the one end portion and the other end portion is preferably larger than the diameter of the central portion.

Provided the maximum outer diameter at the central portion is $D_1$, the maximum outer diameter at the one end portion is $D_2$, and the maximum outer diameter at the other end portion is $D_3$, in the present invention, the maximum outer diameter $D_2$ of the one end portion and the maximum outer diameter $D_3$ of the other end portion are preferably larger than the maximum outer diameter $D_1$ of the central portion. That is, by making the maximum outer diameter $D_1$ at the central portion smaller than the maximum outer diameter $D_2$ at the one end portion and the maximum outer diameter $D_3$ at the other end portion, it is possible to prevent the force for expanding a body lumen from becoming too large, and prevent the body lumen from being damaged.

The maximum outer diameter $D_2$ of the one end portion and the maximum outer diameter $D_3$ of the other end portion may be the same or different. In a case where the maximum outer diameter $D_2$ of the one end portion and the maximum outer diameter $D_3$ of the other end portion are different, the maximum outer diameter $D_3$ of the other end portion may be larger than the maximum outer diameter $D_2$ of the one end portion, or the maximum outer diameter $D_3$ of the other end portion may be smaller than the maximum outer diameter $D_2$ of the one end portion.

The maximum outer diameter $D_1$ of the central portion is appropriately selected based on the diameter of a body lumen in an affected area to be treated. For example, in a case of the self-expanding stent for treatment of a lower extremity artery, the maximum outer diameter $D_1$ of the central portion is 4.0 to 12.0 mm.

The maximum outer diameter $D_2$ of the one end portion and the maximum outer diameter $D_3$ of the other end portion are preferably 0.10 to 2.00 mm larger, more preferably 0.20 to 1.80 mm larger, and still more preferably 0.30 to 1.50 mm larger than the maximum outer diameter $D_1$ of the central portion.

In the tubular medical instrument, annular sections formed to include a wavy constituent that is expandable in a circumferential direction are preferably aligned in an axial direction. The wavy constituent shows the shape of the alphabet V, and the wavy constituents are combined such that the upper and lower sides of the wavy constituents are alternately arranged to have a wavy shape to form the annular section. Provided an acute angle portion (that is, a corner of V, a vertex or bottom of a wave) is a vertex of all parts of the wavy constituent, at least part of the wavy constituent constituting the annular section is preferably connected to at least part of the wavy constituent constituting another adjacent annular section at their vertices.

Then, the annular section in the one end portion is called $A_1$, another annular section adjacent to the annular section $A_1$ is called $A_2$, and the number of connecting portions between the annular section $A_1$ and the annular section $A_2$ is called a. The annular section in the other end portion is called $B_1$, another annular section adjacent to the annular section $B_1$ is called $B_2$, and the number of connecting portions between the annular section $B_1$ and the annular section $B_2$ is called b. The annular section in the central portion is called $C_1$, another annular section adjacent to the annular section $C_1$ is called $C_2$, and the number of connecting portions between the annular section $C_1$ and the annular section $C_2$ is called c. On the above condition, a smaller one of the numbers a and b of the connecting portions is preferably larger than the number c of the connecting portions. By making the numbers a and b of the connecting portions larger than the number c of the connecting portions, the expansion force at the one end portion and the other end portion can be made larger than the expansion force at the central portion.

Preferably, a first annular section of said annular sections at one end of the tubular medical instrument is connected at all vertices to another annular section adjacent to the first annular section, a second annular section of said annular sections at another end of the tubular medical instrument is connected at all vertices to another annular section adjacent to the second annular section, and at least part of the third annular section of said annular sections in the central portion is connected at part of vertices to another annular section adjacent to the third annular section, and is not connected at part of vertices. The annular section connected at all vertices to another adjacent annular section and the annular section including both a vertex connected and a vertex not connected to another adjacent annular section make it possible for the expansion force at the central portion to be smaller than the expansion force at the one end portion and the other end portion.

The central portion of the tubular medical instrument preferably has at least one or more connecting portions connecting opposing vertices of the wavy constituents in adjacent annular sections and at least one or more non-connecting portions not connecting vertices. Further, the number of the non-connecting portions is still more preferably larger than the number of the connecting portions, and the number of the connecting portions is particularly preferably 2 or more and 10 or less.

In the one end portion and in the other end portion of the tubular medical instrument, the number of the connecting portions connecting vertices at which the wavy constituents in adjacent annular sections face each other is preferably 4 or more, more preferably 6 or more, and still more preferably 10 or more. In particular, all vertices at which the wavy constituents in adjacent annular sections face each other are preferably connected.

In the central portion of the tubular medical instrument according to the present invention, in the expansion state, a line connecting adjacent connecting portions connected to each other without another connecting portion interposed between them preferably forms two helices in directions opposite to each other with respect to an axial direction of the tubular medical instrument, and these helices preferably have different wavelengths from each other. Further, the two helices formed in opposite directions with respect to the axial direction preferably have a wavelength ratio of 7:1 to 7:6, more preferably 6:1 to 6:5, and still more preferably 5:1 to 5:4, and most preferably 5:3.

Preferably, in the central portion of the tubular medical instrument of the present invention, the opposing vertices of the wavy constituents in adjacent annular sections are arranged so as to shift from each other with respect to the circumferential direction. That is, the shape of adjacent annular sections the center of which is the connecting portion is preferably asymmetric in an axial direction of the tubular medical instrument. With the different wavelength ratios of the two helices in the opposite directions, along with the asymmetric distribution of the connecting portions, the flexibility is improved and the stress applied to the tubular medical instrument is easily distributed, resulting in further improvement in fatigue durability.

In one end portion and other end portion of the tubular medical instrument according to the present invention, opposing vertices of the wavy constituents in adjacent annular sections are preferably arranged without being shifted from each other in the circumferential direction. That is, the shape of adjacent annular sections the center of which is the connecting portion is preferably symmetric in an axial direction of the tubular medical instrument. The symmetry makes it possible to efficiently transmit the force in the axial direction of the tubular medical instrument, and thus both end portions (that is, one end portion and other end portion) of the tubular medical instrument can be easily pushed and moved without buckling deformation in the transfer device.

The material of the tubular medical instrument is an alloy, and is preferably a shape memory alloy in particular. Although the type of the shape memory alloy is not limited, for example, a nickel-titanium alloy is preferable, and one having a shape memory characteristic and a superelastic characteristic and further being excellent in workability is more preferable. As the nickel-titanium alloy, a nickel-titanium alloy containing about 50% to 60% by mass of nickel with a remaining portion being titanium and unavoidable impurities can be particularly preferably used.

The nickel-titanium alloy is an alloy that reversibly phase-transforms between an austenitic phase (B2 structure) and a martensitic phase (B19' structure). The austenitic phase is a phase having relatively high strength. On the other hand, the martensitic phase is a phase that is easily deformed by external stress, and is a phase that returns to its original state even in a case it receives strain up to about 8%. The strain introduced into the martensitic phase in the alloy to cause a change in shape reverts in a case a reverse phase transformation to the austenitic phase is completed, and, in this manner, the material is restored to its original shape. The normal phase transformation and the reverse phase transformation are caused by stress loading or unloading (superelastic effect), temperature change (shape memory effect), or a combination of these. Note that, in the present description, the term "shape memory alloy" can be used interchangeably with the term "superelastic alloy" to indicate a material suitable for the method of the present invention.

Further, in some nickel-titanium alloys, a normal phase transformation or a reverse phase transformation is shown depending on a temperature and stress between the austenitic phase (B2 structure) stable on a high temperature side and the martensitic phase (B19' structure) having a monoclinic structure stable on a low temperature side. However, a crystal phase of a rhombohedral structure may appear before the austenitic phase transforms to the martensitic phase or before the martensitic phase transforms to the austenitic phase, and this crystal phase is called an R-phase (Rhombohedral phase).

Among shape memory alloys suitably used as a material of the tubular medical instrument according to the present invention, phase transformation of a nickel-titanium alloy will be described in more detail with reference to the drawings. However, the present invention is not limited to the drawings.

FIG. 1 is a graph showing a change in heat quantity in a case the nickel-titanium alloy exhibits a two-step phase transformation. The horizontal axis shows the temperature, and the vertical axis shows the heat quantity. The upper part shows the exothermic peak as the nickel-titanium alloy is cooled, and the lower part shows the endothermic peak as the nickel-titanium alloy is heated.

The graph showing the change in the heat quantity shown in FIG. 1 can be obtained, for example, in accordance with, without limitation to, ASTM F2004-05 "Standard Test Method for Transformation Temperature of Nickel-Titanium Alloys by Thermal Analysis".

At the time of cooling of the nickel-titanium alloy exhibiting the two-step phase transformation, an R-phase transformation start temperature $R_s$ indicates the temperature at which the phase transformation from the austenitic phase to the R-phase is started, and an R-phase transformation finish temperature $R_f$ indicates the temperature at which the phase transformation from the austenitic phase to the R-phase ends. Further, an R-phase transformation peak temperature $R_p$ indicates a peak temperature in an R-phase transformation curve.

At the time of cooling of the nickel-titanium alloy exhibiting the two-step phase transformation, a martensitic phase transformation start temperature $M_s$ indicates the temperature at which the phase transformation from the R-phase to the martensitic phase starts, and a martensitic phase transformation finish temperature $M_f$ indicates the temperature at which the phase transformation from the R-phase to the martensitic phase ends. Further, a martensitic phase transformation peak temperature $M_p$ indicates the peak temperature in a martensitic phase transformation curve.

At the time of cooling of the nickel-titanium alloy exhibiting the two-step phase transformation, the entire shape memory alloy is configured only with the austenitic phase in a temperature range higher than the R-phase transformation start temperature $R_s$. In a temperature range of the R-phase transformation start temperature $R_s$ or less and higher than the R-phase transformation finish temperature $R_f$, the entire shape memory alloy is configured with the austenitic phase and the R-phase. In a temperature range of the R-phase transformation finish temperature $R_f$ or less and higher than the martensitic phase transformation start temperature $M_s$, the entire shape memory alloy is configured only with the R-phase. In a temperature range of the martensitic phase transformation start temperature $M_s$ or less and higher than the martensitic phase transformation finish temperature $M_f$, the entire shape memory alloy is configured with the R-phase and the martensitic phase. In a low temperature range of the martensitic phase transformation finish temperature $M_f$ or less, the entire shape memory alloy is configured only with the martensitic phase.

On the other hand, at the time of heating of the nickel-titanium alloy exhibiting the two-step phase transformation, an R'-phase transformation start temperature $R_s'$ indicates the temperature at which the phase transformation from the martensitic phase to the R-phase is started, and an R'-phase transformation finish temperature $R_f'$ indicates the temperature at which the phase transformation from the martensitic phase to the R-phase ends. Further, an R'-phase transformation peak temperature $R_p'$ indicates a peak temperature in the R-phase transformation curve.

At the time of heating of the nickel-titanium alloy exhibiting the two-step phase transformation, an austenitic phase transformation start temperature $A_s$ indicates the temperature at which the phase transformation from the R-phase to the austenitic phase starts, and an austenitic phase transformation finish temperature $A_f$ indicates the temperature at which the phase transformation from the R-phase to the austenitic phase ends. Further, an austenitic phase transformation peak temperature $A_p$ indicates the peak temperature in an austenitic phase transformation curve.

At the time of heating of the nickel-titanium alloy exhibiting the two-step phase transformation, in a temperature range lower than the R'-phase transformation start temperature the entire shape memory alloy is configured only with the martensitic phase, and in a temperature range of the austenitic phase transformation finish temperature $A_f$ or more, the entire shape memory alloy is configured only with the austenitic phase.

As shown in FIG. 1, the nickel-titanium alloy exhibiting a two-step phase transformation including an R-phase transformation during the phase transformation between the austenitic phase and the martensitic phase used in the tubular medical instrument of the present invention is preferably a symmetrical two-step phase transformation shape memory alloy exhibiting the same number, two, of peaks at the time of heating and at the time of cooling. At the time of cooling, a peak showing a phase transformation from the austenitic phase to the R-phase and a peak showing a phase transformation from the R-phase to the martensitic phase are preferably confirmed. At the time of heating, a peak showing a phase transformation from the martensitic phase to the R-phase and a peak showing a phase transformation from the R-phase to the austenitic phase are preferably confirmed. Note that the peak means an upwardly convex waveform indicating exothermicity appearing at the time of heating and/or a downwardly convex waveform indicating endothermy appearing at the time of cooling in FIG. 1.

In the alloy constituting the tubular medical instrument of the present invention, a difference between the R'-phase transformation finish temperature $R_f'$ and the austenitic phase transformation finish temperature $A_f$ ($A_f-R_f'$; hereinafter, also referred to as the difference X) is 1° C. or more and 12° C. or less at the one end portion and the other end portion, and a difference between the R'-phase transformation finish temperature $R_f'$ and the austenitic phase transformation finish temperature $A_f$ ($A_f-R_f'$; hereinafter, also referred to as the difference Y) is larger than the difference X in the central portion.

By controlling the difference X ($A_f-R_f'$) between the R'-phase transformation finish temperature $R_f'$ and the austenitic phase transformation finish temperature $A_f$ to be within this range for the alloy in one end portion or other end portion of the tubular medical instrument, the tubular medical instrument can be gradually expanded in a temperature range higher than the austenitic phase transformation finish temperature $A_f$. As a result, the tubular medical instrument can be prevented from jumping to be placed with higher accuracy, and also, can be easily ejected from the transfer device for a tubular medical instrument. When the difference X ($A_f-R_f'$) between the R'-phase transformation finish temperature $R_f'$ and the austenitic phase transformation finish temperature $A_f$ is out of the above-mentioned range, a highly variable behavior is shown for each phase transformation in a temperature range higher than the austenitic phase transformation finish temperature $A_f$, and the tubular medical instrument tends to expand rapidly and jump. The difference X ($A_f-R_f'$) between the R'-phase transformation finish temperature $R_f'$ and the austenitic phase transformation finish temperature $A_f$ is preferably 2° C. or more and 10° C. or less, more preferably 3° C. or more and 8° C. or less.

An alloy in the central portion of the tubular medical instrument having the difference Y ($A_f-R_f'$) between the R'-phase transformation finish temperature $R_f'$ and the austenitic phase transformation finish temperature $A_f$ larger than the difference X ($A_f-R_f'$) makes it possible for the expansion force in the central portion smaller than the expansion force in the one end portion or the other end portion when the diameter of the tubular medical instrument is reduced from the diameter expansion state. As a result, an appropriate expansion force can be maintained for a body lumen in which the tubular medical instrument is placed, and the expansion force at the time of diameter expansion from the diameter reduction state of the tubular medical instrument is controlled to be similar to that in one end portion or other end portion to obtain a uniform expansion force over the entire tubular medical instrument, so that the tubular medical instrument can be prevented from jumping to be placed with higher accuracy, and also, can be easily ejected from the transfer device for a tubular medical instrument. The difference Y ($A_f-R_f'$) is preferably 3° C. or more, more preferably 5° C. or more, and still more preferably 8° C. or more larger than the difference X ($A_f-R_f'$).

For the alloy in the one end portion or the other end portion constituting the tubular medical instrument of the present invention, a difference between the R'-phase transformation peak temperature $R_p'$ and the austenitic phase transformation peak temperature $A_p$ ($A_p-R_p'$; hereinafter, may be referred to as the difference Z) preferably satisfies 1° C. or more and 12° C. or less. By appropriately controlling the difference Z ($A_p-R_p'$) between the R'-phase transformation peak temperature $R_p'$ and the austenitic phase transformation peak temperature $A_p$, the tubular medical instrument can be gradually expanded in a temperature range higher than the austenitic phase transformation finish temperature $A_f$. When the difference Z ($A_p-R_p'$) between the R'-phase transformation peak temperature $R_p'$ and the austenitic phase transformation peak temperature $A_p$ is out of the above-mentioned range, a highly variable behavior is shown for each phase transformation in a temperature range higher than the austenitic phase transformation finish temperature $A_f$, and the tubular medical instrument tends to expand rapidly and jump. The difference Z ($A_p-R_p'$) between the R'-phase transformation peak temperature $R_p'$ and the austenitic phase transformation peak temperature $A_p$ is more preferably 2° C. or more and 10° C. or less, still more preferably 3° C. or more and 8° C. or less.

Here, at the time of heating of a general nickel-titanium alloy, which exhibits a two-step phase transformation and has the austenitic phase transformation start temperature $A_s$ higher than the R'-phase transformation finish temperature $R_f'$, the entire shape memory alloy is configured with the martensitic phase and the R-phase in a temperature range of the R'-phase transformation start temperature $R_s'$ or more and lower than the R'-phase transformation finish temperature $R_f'$, the entire shape memory alloy is configured only with the R-phase in a temperature range of the R'-phase transformation finish temperature $R_f'$ or more and lower than the austenitic phase transformation start temperature $A_s$, and the entire shape memory alloy is configured with the R-phase and the austenitic phase in a temperature range of the austenitic phase transformation start temperature $A_s'$ or more and lower than the austenitic phase transformation finish temperature $A_f'$.

However, at the time of heating of the nickel-titanium alloy exhibiting the two-step phase transformation as shown in FIG. 1, the austenitic phase transformation start temperature $A_s$ is lower than the R'-phase transformation finish temperature $R_f'$. As a result, the entire shape memory alloy is configured with the martensitic phase and the R-phase in a temperature range of the R'-phase transformation start temperature $R_s'$ or more and lower than the austenitic phase transformation start temperature $A_s'$, the martensitic phase, the R-phase, and the austenitic phase are formed to coexist in a temperature range of the austenitic phase transformation start temperature A or more and lower than the R'-phase transformation finish temperature $R_f'$, and the entire shape memory alloy is configured with the R-phase and the austenitic phase in a temperature range of the R'-phase transformation finish temperature $R_f'$ or more and lower than the austenitic phase transformation finish temperature $A_f$.

In the alloy constituting the tubular medical instrument according to the present invention, the peak showing a phase transformation from the martensitic phase to the R-phase and the peak showing a phase transformation from the R-phase to the austenitic phase at the time of heating from a temperature range lower than the martensitic phase transformation finish temperature $M_f$ do not necessarily overlap each other at least partially as shown in FIG. 1, and these peaks may be separated from each other. These peaks preferably overlap each other at least partially from the relationship between the R'-phase transformation finish temperature $R_f'$ and the austenitic phase transformation finish temperature $A_f$, and from the relationship between the R'-phase transformation peak temperature $R_p'$ and the austenitic phase transformation peak temperature $A_p$ and the content described below.

When the peak showing the phase transformation from the martensitic phase to the R-phase and the peak showing the phase transformation from the R-phase to the austenitic phase are completely separated, it tends to be difficult to satisfy the relationship between the R'-phase transformation finish temperature $R_f'$ and the austenitic phase transformation finish temperature $A_f$ of the present invention, and also it becomes difficult to satisfy the relationship between the R'-phase transformation peak temperature $R_p'$ and the austenitic phase transformation peak temperature $A_p$, and a highly variable behavior is shown for each phase transformation in a temperature range higher than the austenitic phase transformation finish temperature $A_f$. Accordingly, the tubular medical instrument tends to expand rapidly.

On the other hand, in a case the peak showing the phase transformation from the martensitic phase to the R-phase and the peak showing the phase transformation from the R-phase to the austenitic phase overlap completely and show one peak, only the phase transformation from the martensitic phase to the austenitic phase is dominantly observed, and a stepwise expansion behavior in which the R-phase transformation is partially observed is hardly obtained. That is, a symmetrical two-step phase transformation shape memory alloy in which the same number, two, of peaks are observed at the time of heating and at the time of cooling in a case measurement is performed with a differential scanning calorimeter is preferable.

The alloy in the one end portion or the other end portion constituting the tubular medical instrument of the present invention preferably has the R'-phase transformation finish temperature $R_f'$ higher than the austenitic phase transformation start temperature $A_s$. The R'-phase transformation finish temperature $R_f'$ higher than the austenitic phase transformation start temperature $A_s$ can satisfy the relationship between the R'-phase transformation finish temperature $R_f'$ and the austenitic phase transformation finish temperature $A_f$, and also can satisfy the relationship between the R'-phase transformation peak temperature $R_p'$ and the austenitic phase transformation peak temperature $A_p$.

The alloy in the one end portion or the other end portion constituting the tubular medical instrument of the present invention preferably has the R'-phase transformation finish temperature $R_f'$ higher than the austenitic phase transformation start temperature A within a range of 1° C. or more and 10° C. or less. The R'-phase transformation finish temperature $R_f'$ is higher than the austenitic phase transformation start temperature $A_s$ more preferably within a range of 2° C. or more and 9° C. or less, and still more preferably within a range of 3° C. or more and 8° C. or less.

Described above is the phenomenon that occurs in the state where there is not stress load on the alloy constituting the tubular medical instrument. A phase formed by a temperature change is called a "thermally induced phase" and a phase formed by stress loading is called a "stress induced phase".

FIG. 2 shows changes in stress and strain in a case the nickel-titanium alloy exhibits a two-step phase transformation.

The graph showing the changes in stress and strain shown in FIG. 2 can be obtained, for example, in accordance with ASTM F2516-05 "Standard Test Method for Tension Testing of Nickel-Titanium Superelastic Materials", and if a measurement object has a shape of a tubular medical instrument represented by a self-expanding stent, measurement can be performed by using a radial force measuring machine (for example, "TTR2" manufactured by Blockwise, and the like) described herein. However, the configuration is not limited to these.

As shown in FIG. 2, in the nickel-titanium alloy exhibiting the two-step phase transformation having the characteristics shown in FIG. 1, in a temperature range where an environmental temperature T is higher than the austenitic phase transformation finish temperature $A_f$, in a case stress is applied, first, a normal phase transformation from the austenitic phase to a stress-induced R-phase occurs, and, as stress is further applied, a normal phase transformation to a stress-induced martensitic phase continuously occurs via the R-phase. That is, an aspect similar to expression of a thermally-induced R-phase and/or martensitic phase by cooling is obtained. After that, in a reversed manner, in a case stress is unloaded, a reverse phase transformation from the stress-induced martensitic phase to the austenitic phase passing little through the R-phase, and the reverse phase transformation from the stress-induced R-phase to the austenitic phase occur in competition. That is, as shown in FIG. 2, in the phase transformation between the austenitic phase and the martensitic phase, the behavior of the reverse phase transformation via the R-phase transformation becomes ambiguous, so that a highly variable behavior is not exhibited for each phase transformation, and a stepwise recovery behavior is shown as compared with a conventionally general nickel-titanium alloy exhibiting a two-step phase transformation. Note that, in a case stress is further unloaded, all crystal phases finally return to the austenitic phase, and thus the shape is completely recovered.

When applied to the tubular medical instrument according to the present invention, in a case an outer shaft and an inner shaft are moved relatively, and the tubular medical instrument is released from the inside of the transfer device at a target affected area in a body lumen and disposed, since the tubular medical instrument is gradually expanded, the tubular medical instrument can be suppressed from bouncing or being deformed, and the tubular medical instrument can be accurately placed at the affected area. Further, since the wavy constituents constituting the tubular medical instrument are arranged in the axial direction by keeping equal distances, the expansion uniformity of the tubular medical instrument is secured, and the expansion maintenance capability and fatigue durability originally provided can be sufficiently expressed.

Further, in the nickel-titanium alloy, if stress is applied in a temperature range where the environmental temperature T is higher than the R'-phase transformation finish temperature $R_f'$ and lower than the austenitic phase transformation finish temperature $A_f$ and the stress-induced R-phase and/or martensitic phase is formed at least partially (that is, an aspect similar to expression of a thermally-induced R-phase and/or martensitic phase by cooling is obtained), in a process of unloading stress after the above, the shape is not completely recovered since not all phases are reverse-phase transformed to the austenitic phase. However, at least all crystal phases are reverse-phase transformed up to the R-phase, and the shape is finally recovered almost completely. Such a shape recovery characteristic is shown, because the transformation strain, a temperature hysteresis, and a stress hysteresis in the phase transformation between the austenitic phase and the R-phase are extremely small compared to those in the phase transformation between the austenitic phase and the martensitic phase.

In contrast, in the nickel-titanium alloy, if stress is applied in a temperature range where the environmental temperature T is higher than the austenitic phase transformation start temperature $A_s$ and lower than the R'-phase transformation finish temperature $R_f'$ and the stress-induced R-phase and/or martensitic phase is formed at least partially (that is, an aspect similar to expression of a thermally-induced R-phase and/or martensitic phase by cooling is obtained), in a process of unloading stress after the above, the stress-induced martensitic phase may be partially reverse-phase transformed up to the austenitic phase. However, since the R-phase does not reverse-phase transformed completely, the shape is not finally recovered completely.

Further, in the nickel-titanium alloy, if stress is applied in a temperature range where the environmental temperature T is higher than the R'-phase transformation start temperature $R_s'$ and lower than the austenitic phase transformation start temperature $A_s$, and the stress-induced R-phase and/or martensitic phase is formed at least partially (that is, an aspect similar to expression of a thermally-induced R-phase and/or martensitic phase by cooling is obtained), in a process of unloading stress after the above, the stress-induced martensitic phase is not reverse-phase transformed to the austenitic phase. As a result, since reverse phase transformation is not performed up to the R-phase completely, the shape is not finally recovered completely.

Note that, in a temperature range where the environmental temperature T is lower than the R-phase transformation finish temperature $R_f$ by cooling, all crystal phases of the shape memory alloy have already been configured with the thermally-induced R-phase or martensitic phase under no stress. Therefore, even if stress is applied, the stress-induced R-phase is not expressed, and only the stress-induced martensitic phase is expressed.

In a temperature range where the environmental temperature T is lower than the martensitic phase transformation finish temperature $M_f$ by further cooling, all crystal phase of the shape memory alloy have already been configured with the martensitic phase under no stress, and thus an effect of no-shape recovery is maximized.

As described above, the alloy constituting the tubular medical instrument of the present invention has the austenitic phase transformation finish temperature $A_f$ of a body temperature or less. The austenitic phase transformation finish temperature $A_f$ of a body temperature or less enables a superelastic characteristic to be expressed at the body temperature. The body temperature means 37° C., and the austenitic phase transformation finish temperature $A_f$ is preferably 15° C. or more and 37° C. or less, more preferably 20° C. or more and 35° C. or less, and still more preferably 22° C. or more and 33° C. or less.

As described above, in the alloy constituting the tubular medical instrument, at the time of heating, the peak showing the phase transformation from the martensitic phase to the R-phase and the peak showing the phase transformation from the R-phase to the austenitic phase may overlap each other at least partially. For this reason, for example, in the test method described in ASTM F2004-05, it may be difficult to define the austenitic phase transformation start temperature $A_s$ and the R'-phase transformation finish temperature $R_f'$. In view of the above, in the present invention, the austenitic phase transformation start temperature $A_s$ and the R'-phase transformation finish temperature $R_f'$ are preferably defined by a method described below.

In a first method, cooling is first performed from a temperature range higher than the austenitic phase transformation finish temperature $A_f$ to a temperature range lower than the martensitic phase transformation finish temperature $M_f$, and then heating is performed to a temperature range higher than the austenitic phase transformation finish temperature $A_f$, to obtain a graph of the relationship between a temperature and heat quantity exhibiting two-step phase transformation. Next, with respect to partial overlapping of a peak showing a phase transformation from a martensitic phase to an R-phase and a peak showing a phase transformation from the R-phase to an austenitic phase which appear at the time of heating in the obtained graph showing the relationship between a temperature and heat quantity, for example, software for data analysis, such as Excel, Origin, Igor, SigmaPlot, or the like, is used, and based on an optional peak fitting function or the like, the peaks are separated. In this manner, the austenitic phase transformation start temperature $A_s$ and the R'-phase transformation finish temperature $R_f'$ can be defined.

As a second method, there is the method of analyzing a phase transformation characteristic of a shape memory material described in WO 2009/073611. By using this method, the austenitic phase transformation start temperature $A_s$ and the R'-phase transformation finish temperature $R_f'$ can be determined.

The nickel-titanium alloy itself is commercially available or can be manufactured by a publicly-known method. For example, the nickel-titanium alloy exhibiting a two-step phase transformation can be obtained by applying heat treatment described below.

In order for the nickel-titanium alloy to exhibit the R-phase transformation, a nickel-rich composition such as, for example, about 51 atomic % nickel and about 49 atomic % titanium is preferably selected as a molten material. In addition, one or more alloying additive elements (for example, ternary or quaternary elements, such as iron) may be included in the shape memory alloy composition. After cold working, heat treatment may be performed at about 400° C. or more and about 550° C. or less. By using these methods, martensitic phase transformation can be suppressed with respect to R-phase transformation.

Further, with respect to an alloy in the one end portion or the other end portion of the tubular medical instrument, in order to satisfy the relationship between the R'-phase transformation finish temperature $R_f'$ and the austenitic phase transformation finish temperature $A_f$, and the relationship between the R'-phase transformation peak temperature $R_p'$ and the austenitic phase transformation peak temperature $A_p$, after cold working a nickel-titanium alloy with the austenitic phase transformation finish temperature $A_f$ of preferably 0° C. or less, heat treatment is preferably performed at 480° C. or more and 500° C. or less. The heat treatment is more preferably performed at 485° C. or more and 495° C. or less.

With respect to the alloy in the one end portion or the other end portion of the tubular medical instrument, it is preferable to perform the heat treatment a plurality of times after cold working. The number of times of heat treatments is preferably 2 or more and 20 or less, more preferably 3 or more and 15 or less, and still more preferably 4 or more and 10 or less.

In the heat treatment of the alloy in the one end portion or the other end portion of the tubular medical instrument, a total period of heat treatment time is preferably 5 minutes or more and 60 minutes or less, more preferably 10 minutes or more and 45 minutes or less, and still more preferably 15 minutes or more and 30 minutes or less.

On the other hand, with respect to an alloy in the central portion of the tubular medical instrument, in order to satisfy the relationship between the R'-phase transformation finish temperature $R_f'$ and the austenitic phase transformation finish temperature $A_f$, and the relationship between the R'-phase transformation peak temperature $R_p'$ and the austenitic phase transformation peak temperature $A_p$, after cold working a nickel-titanium alloy with the austenitic phase transformation finish temperature $A_f$ of preferably 0° C. or less, heat treatment is preferably performed at a temperature lower than the temperature of the heat treatment performed for the alloy in the one end portion and in the other end portion. The heat treatment temperature is more preferably, for example, 5° C. or more lower, still more preferably 10° C. or more lower than the temperature of the heat treatment performed for the alloy in the central portion. The heat treatment temperature is, for example, preferably 400° C. or more and 500° C. or less, and more preferably 450° C. or more and 480° C. or less.

With respect to the alloy in the central portion of the tubular medical instrument, after cold working, the heat treatment may be performed in one time or may be performed in a plurality of times. The number of times of the heat treatments is preferably 1 or more and 10 or less, more preferably 1 or more and 7 or less, and still more preferably 1 or more and 5 or less.

In the heat treatment of the alloy in the central portion of the tubular medical instrument, a total period of heat treatment time is preferably 1 minute or more and 30 minutes or less, more preferably 2 minutes or more and 15 minutes or less, and still more preferably 3 minutes or more and 10 minutes or less.

The alloy of the tubular medical instrument (that is, the alloy in a one end portion, the other end portion, and a central portion) may be cooled to normal temperature after the heat treatment, and the cooling rate does not have a large influence on the transformation temperature of the nickel-titanium alloy. Accordingly, a publicly-known method can be selected appropriately. For cooling, for example, methods such as water cooling, oil cooling, air cooling, furnace cooling, and the like can be appropriately selected. From the viewpoint of stabilizing the quality, the cooling rate is preferably controlled, and, for the alloy in the one end portion or the other end portion of the tubular medical instrument, an average cooling rate at the time of cooling is preferably 1° C./min or more and 200° C. or less, more preferably 5° C./min or more and 150° C./min or less, and still more preferably 10° C./min or more and 100° C./min or less. On the other hand, with respect to the alloy in the central portion of the tubular medical instrument, the average cooling rate at the time of cooling may be in the same range as that for the alloy in the one end portion or the other end portion of the tubular medical instrument. However, the cooling is more preferably performed at a higher rate. In order to increase the cooling rate, a method of rapid cooling by contacting a cooling medium, such as water, after the heat treatment can be preferably employed.

A range of the heat treatment temperature, the number of times of the heat treatment, the heat treatment time, and the average cooling rate in the heat treatment is determined such that the austenitic phase transformation finish temperature $A_f$ is a body temperature or less, and the positional relationship between a peak showing phase transformation from the martensitic phase to the R-phase and phase transformation from the R-phase to the austenitic phase can be adjusted.

Although a heat treat furnace used for the heat treatment is not limited as long as the heat treat furnace can achieve the temperature range, and, for example, a salt bath furnace or a fluidized bed furnace can be used preferably. Since these furnaces have small irregularities of the temperature distribution and a small temperature change due to insertion and removal of a work, a temperature of the nickel-titanium alloy at the time of heat treatment can be strictly controlled.

Note that the crystal phase of the nickel-titanium alloy can be identified by using an analysis method, such as an X-ray diffraction method (XRD) or the like.

The tubular medical instrument provided with the alloy in the one end portion or the other end portion and the alloy in the central portion can be manufactured by being applied with different heat treatment conditions by using, for example, a molding system including a temperature-controllable mold for each portion. As another method, there is a method of forming the tubular medical instrument, in which, after portions of the tubular medical instrument containing the alloys are formed by being applied with heat treatment separately, these portions are combined by methods, such as welding, brazing, bonding, and the like, or are integrated by methods, such as braiding, knitting, and the like. However, the present invention is not limited to the above methods as long as the heat treatment can be performed for the tubular medical instrument provided with the alloy in the one end portion or the other end portion and the alloy in the central portion.

The above object of the present invention can be achieved even with a tubular medical instrument comprises one end portion, the other end portion, and a central portion, wherein the one end portion is a region including one axial end of the tubular medical instrument and having a length of 10% with respect to an axial length $L_1$ of the tubular medical instrument, the other end portion is a region including the other axial end of the tubular medical instrument and having a length of 10% with respect to the axial length $L_1$ of the tubular medical instrument, the central portion is a region including an axial center of the tubular medical instrument and having a length of 10% with respect to the axial length $L_1$ of the tubular medical instrument, and a ratio (difference V/difference W) calculated by the following test method is 3 or more: the tubular medical instrument is subjected to a contraction-expansion cycle where the tubular medical instrument is contracted from an expanded state to a contracted state such that an average diameter of the tubular instrument becomes 25%, and then allowed to expand from the contracted state to the expanded state, wherein the difference V is a difference between an expansion force per unit length in the radial direction in the central portion and an expansion force per unit length in the radial direction in the one end portion or the other end portion, whichever is smaller, at the time when the average diameter becomes 75% as the tubular medical instrument is being contracted from the expanded state such that the average diameter of the tubular instrument becomes 25%, and the difference W is a difference between an expansion force per unit length in the radial direction in the central portion and an expansion force per unit in the radial direction in the one end portion or the other end portion, whichever is smaller, at the time when the average diameter becomes 75% as the tubular medical instrument is being allowed to expanded from the contracted state.

A ratio (difference V/difference W) calculated by the test method will be described with reference to FIG. 3. FIG. 3 is a schematic diagram showing a relationship between an average diameter of the tubular medical instrument and an expansion force per unit length in a radial direction, provided that an average diameter of the tubular medical instrument is 100%, and, after diameter reduction is performed such that the average diameter of the tubular medical instrument becomes 25%, diameter expansion is performed such that the average diameter becomes at least 75%. In FIG. 3, a solid line shows a result at the end portion of the tubular medical instrument and a dotted line shows a result in the central portion of the tubular medical instrument.

As shown in FIG. 3, in the tubular medical instrument of the present invention, at the time of diameter reduction, the expansion force at the end portion is preferably relatively larger than the expansion force in the central portion, and, at the time of diameter expansion, the expansion force at the end portion and the expansion force in the central portion are preferably substantially equal. By making the expansion force at the end portion at the time of diameter reduction relatively larger than the expansion force in the central portion, it is possible to prevent the tubular medical instrument placed in an affected area from moving and being shifted from the affected area. Further, by making the expansion force at the end portion and the expansion force in the central portion at the time of diameter reduction substantially equal, it is possible to prevent the jumping in a case the tubular medical instrument is ejected from the inside of the transfer device. Accordingly, the tubular medical instrument can be accurately placed at the affected area. In view of the above, in the present invention, the difference V obtained by subtracting an expansion force per unit length in the radial direction in the central portion from a smaller one of expansion force per unit length in the radial direction at the one end portion or the other end portion at a time point at which the average diameter of the tubular medical instrument becomes 75% in a case diameter reduction is performed such that the average diameter of the tubular medical instrument becomes 25%, and the difference W obtained by subtracting an expansion force per unit length in the radial direction in the central portion from a smaller one of expansion force per unit length in the radial direction at the one end portion or the other end portion at a time point at which the average diameter of the tubular medical instrument becomes 75% in a case diameter expansion is performed such that the average diameter becomes at least 75% after diameter reduction are obtained, and a ratio of these differences (difference V/difference W) is 3 or more. The ratio is preferably 4 or more, or more preferably 5 or more. An upper limit of the ratio is not particularly limited, and is preferably 10 or less, more preferably 9 or less, and still more preferably 8 or less.

In order to make the ratio in the tubular medical instrument of the present invention be 3 or more, types of the alloy used for the one end portion or the other end portion of the tubular medical instrument and the alloy used for the central portion are preferably changed, or the heat treatment conditions applied to the alloy are preferably changed. Further, the structures at the one end portion or the other end portion of the tubular medical instrument and the central portion are preferably changed. Specifically, as the alloy constituting the one end portion or the other end portion of the tubular medical instrument, one, in which the difference X between the R'-phase transformation finish temperature $R_f'$ and the austenitic phase transformation finish temperature $A_f$ ($A_f$-$R_f$) is 1° C. or more and 12° C. or less, is preferably used, and as the alloy constituting the central portion of the tubular medical instrument, one, in which the difference Y between the R'-phase transformation finish temperature $R_f'$ and the austenitic phase transformation finish temperature $A_f$ ($A_f$-$R_f'$) is larger than the difference X, is preferably used. Further, the tubular medical instrument preferably has a structure in which annular sections formed to include the wavy constituent expandable in a circumferential direction are aligned in an axial direction, and, a number a, a number b, and a number c are defined as follows and the number a or the number b, whichever is smaller, is larger than the number c, and where the number a is defined as a number of connecting portions between an annular section $A_1$ in the one end portion and another annular section $A_2$ adjacent to the annular section $A_1$, the number b is defined as a number of connecting portions between an annular section $B_1$ in the other end portion and another annular section $B_2$ adjacent to the annular section $B_1$, and the number c is defined as a number of connecting portions between an annular section $C_1$ in the central portion and another annular section $C_2$ adjacent to the annular section $C_1$.

As described above, the tubular medical instrument of the present invention appropriately controls the expansion force in a central portion, one end portion, and other end portion. Accordingly, while the flexibility and the fatigue durability are improved, the tubular medical instrument has a sufficient expansion force that allows restriction of movement from an affected area and restenosis, and can be easily pushed and moved in the transfer device without buckling deformation. As a result, the tubular medical instrument can be easily ejected from the transfer device, and the tubular medical instrument released from the inside of a lumen of the transfer device can be accurately placed at an affected area.

The design of the tubular medical instrument of the present invention is not limited to the above, and the expansion force can be appropriately adjusted, for example, by adjusting a length and an angle of a strut constituting the wavy constituent in each annular section. As another design of the tubular medical instrument, for example, the entire content proposed in WO 2010/029928 is cited in the present invention.

Specifically, the tubular medical instruments include a stent, a stent graft, an obturator, an injection catheter, a prosthetic valve, and the like. In particular, the tubular medical instrument of the present invention is preferably a stent.

Although description will be made on a stent hereinafter, it does not mean that the tubular medical instrument according to the present invention is limited to a stent.

The form of the stent is not particularly limited. For example, (a) a coiled stent including a single linear alloy, (b) a stent obtained by cutting an alloy tube by laser, (c) a stent assembled by welding a linear member by laser, (d) a stent made by weaving a plurality of linear alloys, and the like are included.

The stent preferably has a mesh structure portion.

In general, the stents can be classified, based on the expansion mechanism, into (i) a balloon expandable stent, in which a stent is mounted on an outer surface of a balloon and transferred to an affected area, and the stent is expanded by the balloon at the affected area, and (ii) a self-expanding stent, in which a stent is loaded on a catheter having a sheath member that suppresses the expansion of the stent and transferred to an affected area, and the sheath member is removed at the affected area to expand the stent by itself. In particular, the tubular medical instrument of the present invention is preferably a self-expanding stent.

Although description will be made on a self-expanding stent hereinafter, it does not mean that the tubular medical instrument according to the present invention is limited to a self-expanding stent.

FIG. 4 is a schematic view for describing a self-expanding stent as one form of the tubular medical instrument according to the present invention, and FIG. 5 shows a cross-sectional view in a case a self-expanding stent in the expanded state is cut in parallel with the axial direction.

A self-expanding stent 11 is formed into a tubular body, in which annular sections 12 formed to include a wavy constituent 13 that is expandable in a circumferential direction are formed to be aligned in an axial direction. In FIG. 4, 19 of the annular sections 12 are aligned.

At least part of the wavy constituent 13 constituting the annular section 12 is connected at vertices to at least part of the wavy constituent constituting another adjacent one of the annular section to form a connecting portion 14.

With respect to the self-expanding stent 11 shown in FIG. 4, provided a left end is one end and a right end is other end, a strong region 15 including the one end portion is configured with 2 of the annular sections, a weak region 16 including a central portion is configured with 15 of the annular sections, and a strong region 17 including other end portion is configured with 2 of the annular sections aligned in an axial direction.

Provided that the maximum outer diameter of the central portion in the weak region 16 is $D_1$, the maximum outer diameter of the one end portion in the strong region 15 is $D_2$, and the maximum outer diameter of the other end portion in the strong region 17 is $D_3$, the maximum outer diameter $D_2$ of the one end portion and the maximum outer diameter $D_3$ of the other end portion are larger than the maximum outer diameter $D_1$ of the central portion.

Note that, in FIG. 4, the axial length of the self-expanding stent 11 is indicated by $L_1$.

The strong region 15 or the strong region 17 of the tubular medical instrument preferably has a flare shape in which the diameter is expanded toward the one end or the other end of the self-expanding stent, as shown in FIG. 4. By forming the flare shape, the change in magnitude of the expansion force from the weak region 16 to the strong region 15 or the strong region 17 of the self-expanding stent 11 becomes continuous, so that both end portions (the strong region 15 and the strong region 17) of the self-expanding stent 11 in the transfer device can be pushed and moved without causing buckling deformation, and movement or restenosis of the self-expanding stent 11 after being placed at an affected area can be suppressed from occurring frequently.

The self-expanding stent 11 can be manufactured, for example, by expanding a diameter of a nickel-titanium alloy pipe applied with laser cutting, performing heat treatment to form a desired shape, and finally electropolishing.

FIG. 5 shows a developed view of the self-expanding stent 11 shown in FIG. 4 in the expanded state. In the self-expanding stent 11 shown in FIG. 5, the number a of joints between an annular section $A_1$ in the strong region 15 and another annular section $A_2$ adjacent to the annular section $A_1$ is 16. The number b of joints between an annular section $B_1$ in the strong region 17 and another annular section $B_2$ adjacent to the annular section $B_1$ is 16. The number c of joints between an annular section $C_1$ in the weak region 16 and another annular section $C_2$ adjacent to the annular section $C_1$ is 4.

FIG. 6 is a schematic view showing the wavy constituent 13 constituting the self-expanding stent 11 shown in FIG. 4. The wavy constituent 13 has a shape of an alphabet V as shown in FIG. 6.

FIG. 7 is a schematic view showing the connecting portion 14 of adjacent ones of the wavy constituents 13 of the self-expanding stent 11 shown in FIG. 4. As shown in FIG. 7, vertices 37 of the adjacent ones of the wavy constituents 13 are joined to form the connecting portion 14.

<Transfer Device for a Tubular Medical Instrument>

Next, a transfer device for a tubular medical instrument having the tubular medical instrument will be described.

Hereinafter, a self-expanding stent will be mentioned as the tubular medical instrument, and a catheter structure of the Over-The-Wire (OTW) type which is generally used as a device for transferring a self-expanding stent will be described using FIGS. 8 and 9. However, the present invention is not limited to the above. As for the catheter structure, for example, in addition to the OTW type, a catheter structure of the Rapid-Exchange (RX) type is also generally known.

FIG. 8 shows a general view of a transfer device for a tubular medical instrument 71 having the self-expanding stent 11. FIG. 8 shows a state in which the self-expanding stent 11 is stored in a lumen of an outer shaft 72. FIG. 9 is a schematic view showing a state in which the self-expanding stent 11 is released from the transfer device for a tubular medical instrument 71.

The transfer device for a tubular medical instrument 71 having a self-expanding stent is a device for transferring the self-expanding stent 11 to an affected area (for example, a stenosis site) of a body lumen. The transfer device for a tubular medical instrument 71 is elongated and flexible so that it can be inserted into a body lumen.

The transfer device for a tubular medical instrument 71 preferably has the outer shaft 72 having a lumen, the self-expanding stent 11 stored in the lumen of the outer shaft 72, and an inner shaft 73 disposed in a lumen of the self-expanding stent 11. The outer shaft 72 stores the self-expanding stent 11 as an outer diameter in a contracted state (=an inner diameter of the outer shaft 72). When the holding by the outer shaft 72 is released, the outer diameter of the self-expanding stent 11 in the contracted state is expanded to be the outer diameter of the outer shaft 72 or more, and the outer diameter after expansion is determined.

The transfer device for a tubular medical instrument 71 is stored in a state where the self-expanding stent 11 is contracted. More specifically, by using a stent contraction device, the entire stent is uniformly contracted from the radial direction to be the inner diameter of the outer shaft 72 or less, and loaded into the lumen of the outer shaft 72. As the stent contraction device, for example, a device commercially available from MSI, Blockwise, or the like can be used.

The self-expanding stent 11 can be loaded, for example, by pushing the self-expanding stent contracted by the stent contraction device with a push rod, and feeding it into the lumen of the outer shaft 72. Note that the self-expanding stent 11 may be fed into the lumen of the outer shaft 72 by a method publicly-known to those skilled in the art, other than by pushing with the push rod.

The environmental temperature T in a case the self-expanding stent 11 is loaded into the lumen of the outer shaft 72 is preferably lower than the R'-phase transformation finish temperature $R_f'$. The environmental temperature T lower than the R'-phase transformation finish temperature $R_f'$ can prevent the shape from completely recovering as the stress is unloaded. Accordingly, a force to expand from a state in which a diameter of the self-expanding stent 11 is reduced by applying stress becomes small. Therefore, the resistance load as the self-expanding stent 11 is loaded into the outer shaft 72 can be made smaller than in other temperature ranges, which is extremely effective. The environmental temperature T as the self-expanding stent 11 is loaded into the lumen of the outer shaft 72 is more preferably a temperature lower than the R-phase transformation finish temperature $R_f$, and still more preferably higher than the martensitic phase transformation start temperature $M_s$ and lower than the R-phase transformation finish temperature $R_f$.

At a temperature where the environmental temperature T is lower than the R-phase transformation finish temperature $R_f$, all crystal phases of the shape memory alloy have already been configured with a thermally-induced R-phase or martensitic phase under no stress. In particular, at a temperature higher than the martensitic phase transformation start temperature $M_s$ and lower than the R-phase transformation finish temperature $R_f$, all the crystal phases of the shape memory alloy have already been configured with a thermally-induced R-phase under no stress. For this reason, even if stress is applied, a stress-induced R-phase does not appear, and only a stress-induced martensitic phase is expressed. As a result, in a relatively high temperature range, a force to expand from a state in which a diameter of the self-expanding stent 11 is reduced by applying stress becomes small, and the resistance load as the self-expanding stent 11 is loaded into the outer shaft 72 can be made small as compared with other temperature ranges. Accordingly, the configuration is extremely effective.

Conventionally, in order to reduce a resistance force at the time of loading, it has been necessary to perform cooling to at least a temperature at which the martensitic phase is expressed, particularly to a temperature range lower than the martensitic phase transformation finish temperature $M_f$, which is a temperature range that requires liquid nitrogen. For this reason, the operation has been troublesome, and a special facility has been required. However, by loading the self-expanding stent 11 into the outer shaft 72 at a temperature lower than the R'-phase transformation finish temperature $R_f'$, particularly at a temperature higher than the martensitic phase transformation start temperature $M_s$ and lower than the R-phase transformation finish temperature $R_f$, the resistance force at the time of loading can be effectively reduced in a temperature range that is easy for operation.

(Outer Shaft)

The outer shaft 72 is preferably formed of a member having flexibility and kink resistance enough to follow a lumen (such as a blood vessel) into which the shaft is inserted, and a tensile strength to the degree at which the shaft does not extend in a case the transfer device for a tubular medical instrument 71 is pulled during a procedure. On an inner side of the outer shaft 72, a layer that has low friction is preferably formed, so that the movement resistance (sliding resistance) with the self-expanding stent 11 in contact with an inner circumferential surface can be reduced, and the outer shaft 72 can be easily moved. From the viewpoint of satisfying such a characteristic, for example, an outer layer and an inner layer of the outer shaft 72 are preferably formed of resin. Further, the outer shaft 72 is preferably formed of a three-layer resin-metal composite tube, in which a layer including a metal wire is embedded as a reinforcing layer between the outer layer and the inner layer.

Examples of the resin used for the outer layer include polyethylene, fluorine resin, such as PTFE and PFA, polyamide, polyamide elastomer, polyurethane, polyester, or elastic resin, such as silicone. Examples of the resin used for the inner layer include low friction resin, such as polyethylene and fluorine resin, such as PTFE and PFA. Examples of the metal wire constituting the reinforcing layer include metal wires of steel, such as stainless steel, a nickel-titanium alloy, tungsten, gold, platinum, or the like. Note that the metal wire preferably forms at least one of a braided structure and a coil structure, and preferably forms such a structure from a proximal end to a distal end of the outer shaft 72. Note that the proximal end means the side of a hand of an operator, and the distal end means the opposite side of the proximal end, that is, the side closer to an affected area or the like.

A portion of the outer shaft 72 in the vicinity of a place where the self-expanding stent 11 is stored may be formed of a single-layer tube. Examples of the resin used for the tube include low friction resin, such as polyethylene and fluorine resin, such as PTFE and PFA.

(Inner Shaft)

The inner shaft 73 is a tubular member having a lumen through which a guide wire passes, and a pusher member 74 is preferably attached to a proximal side of the self-expanding stent 11, a front end tip 75 is preferably attached to a distal side of the inner shaft 73, and an operation member 76 is preferably attached to the side of a hand of an operator.

At least part of the tubular member having a lumen through which the guide wire passes is inserted into the lumen of the outer shaft 72. Then, the guide wire is inserted into the lumen formed in the inner shaft 73 to guide the transfer device for a tubular medical instrument 71 to an affected area.

The inner shaft 73 preferably has flexibility and kink resistance enough to follow a lumen (that is, a lumen inserted into a body lumen) of the outer shaft 72, and a tensile strength to the degree at which the inner shaft 73 does not extend in a case a catheter is pulled during a procedure.

The inner shaft 73 is preferably formed of resin. Examples of the resin include polyethylene, fluorine resin, such as PTFE and PFA, polyamide, polyamide elastomer, polyurethane, polyester, polyimide, or resin, such as silicone.

The inner shaft 73 is preferably reinforced by metal. Examples of the reinforcing material include metal of steel, such as stainless steel, a nickel-titanium alloy, tungsten, gold, platinum, or the like.

(Tubular Member)

A tubular member 81 is preferably interposed between the inner shaft 73 and the self-expanding stent 11. The tubular member 81 may be hereinafter referred to as an anti jumping layer 81. By interposing the anti jumping layer 81, as shown in FIG. 9, an angle θ formed by the self-expanding stent 11 and the anti jumping layer 81 can be reduced in a case the outer shaft 72 and the inner shaft 73 are moved relative to each other to release the self-expanding stent 11 from the inside of the transfer device for a tubular medical instrument 71 and placed at a target affected area in a body lumen. As a result, the self-expanding stent 11 is expanded gradually, and jumping and deformation of the self-expanding stent 11 can be suppressed, and the placement accuracy can be enhanced. Further, since the wavy constituents 13 adjacent to each other in the axial direction constituting the self-expanding stent 11 are placed at equal distances, the expansion uniformity of the self-expanding stent 11 is ensured, and the expansion maintenance capability and the fatigue durability that is originally provided can be sufficiently expressed.

The anti jumping layer 81 is preferably interposed on an inner side of at least one of the strong region 15 and the strong region 17 of the self-expanding stent 11. The anti jumping layer 81 is preferably interposed partially or entirely in the strong region 15 or the strong region 17.

A difference between the inner diameter of the self-expanding stent 11 stored in the lumen of the outer shaft 72 and the outer diameter of the anti jumping layer 81 is preferably 0.05 mm or more and 0.35 mm or less. When the difference is less than 0.05 mm, a channel of a saline solution or the like is difficult to be secured in a case operation of filling a lumen of the transfer device for a tubular medical instrument 71 with the saline solution or the like to eliminate an air bubble (sometimes called flushing) is performed. For this reason, it becomes difficult to remove an air bubble. On the other hand, in a case the difference exceeds 0.35 mm, the jumping phenomenon easily occurs as the self-expanding stent 11 is released from the inside of the transfer device for a tubular medical instrument 71 and placed at an affected area. The difference is preferably 0.05 mm or more and 0.35 mm or less, more preferably 0.10 mm or more and 0.30 mm or less, and still more preferably 0.15 mm or more and 0.25 mm or less.

As the anti jumping layer 81, for example, those exemplified as the resin constituting the inner shaft 73 can be used. In particular, in order to hold the self-expanding stent 11 at least temporarily by frictional contact or the like as the self-expanding stent 11 is released from the inside of the transfer device for a tubular medical instrument 71 and placed at an affected area, a material having flexibility or tackiness is preferably used, and, in particular, resin having a Shore D hardness of 25 to 72 can be preferably used.

(Pusher Member)

The pusher member 74 is preferably mounted around the inner shaft 73. The pusher member 74 may have size that fits within the lumen of the outer shaft 72. The pusher member 74 is preferably adhered or welded around the inner shaft 73, for example.

By providing the pusher member 74, the self-expanding stent 11 can be ejected from the outer shaft 72 according to the relative movement of the outer shaft 72 and the inner shaft 73.

The shape of the pusher member 74 is, for example, a ring shape, and the outer diameter of the pusher member 74 is preferably the inner diameter of the contracted self-expanding stent 11 or more and the inner diameter of the outer shaft 72 or less. With such a size, the pusher member 74 can be pushed out over the peripheral edge at the end portion of the self-expanding stent 11, so that the self-expanding stent 11 can be efficiently ejected.

Examples of a material of the pusher member 74 include polyethylene, fluorine resin, such as PTFE and PFA, polyamide, polyamide elastomer, polyurethane, polyester, or resin, such as silicone.

Preferably, the pusher member 74 includes at least partially a radiopaque material. The radiopaque material enables the self-expanding stent 11 stored in the transfer device for a tubular medical instrument 71 to be transferred safely and efficiently to an affected area in a body lumen under fluoroscopy, and ejected. Note that the radiopaque material may be, for example, a contrast material, such as an X-ray contrast material or an ultrasound contrast material. Specifically, examples of the radiopaque material include gold, platinum, tungsten, tantalum, iridium, palladium, or an alloy of these, or a gold-palladium alloy, platinum-iridium, NiTiPd, NiTiAu, barium sulfate, a bismuth compound, or a tungsten compound.

(Front End Tip)

The front end tip 75 is attached to a front end of the inner shaft 73. By providing the front end tip 75, for example, the transfer device for a tubular medical instrument 71 can easily pass through an affected area, such as a stenosis site. The front end tip 75 is preferably attached to the front end of the inner shaft 73 by, for example, adhesion or welding.

The front end tip 75 is preferably made from a material having flexibility to follow a lumen, such as a blood vessel, into which the front end tip 75 is inserted, and having rigidity in the axial direction that allows the front end tip 75 to pass through a stenosis site. Examples of a material of the front end tip 75 include polyethylene, fluorine resin, such as PTFE and PFA, polyamide, polyamide elastomer, polyurethane, polyester, or resin, such as silicone.

Preferably, the front end tip 75 includes at least partially a radiopaque material. The radiopaque material enables the self-expanding stent 11 stored in the transfer device for a tubular medical instrument 71 to be transferred safely and efficiently to an affected area in a body lumen under fluoroscopy, and ejected. As the radiopaque material, those exemplified as the material of the pusher member 74 can be used.

(Operation Member)

The operation member 76 is attached to a proximal end of the inner shaft 73. Specifically, the operation member 76 is preferably attached by adhesion or welding.

The shape of the operation member 76 is not particularly limited as long as it is a shape that is easy for the operator to operate, however, for example, as shown in FIG. 8, is preferably a shape including a holding part that can be held by hand.

Examples of the material of the operation member 76 include metal such as steel including stainless steel, aluminum, iron, nickel, and titanium; and resin such as polyether ether ketone, polyamide, polyimide, and polycarbonate.

As described above, although the tubular medical instrument and the transfer device for a tubular medical instrument according to the present invention are described using specific examples, the present invention is not limited by the above embodiments. The present invention can be implemented by making a change within a range conforming to the gist described above or later, and all such modifications are included in the technical scope of the present invention.

The present application claims benefit of priority based on Japanese Patent Application No. 2017-134170 filed on Jul. 7, 2017. The descriptions of Japanese Patent Application No. 2017-134170 is incorporated herein by reference in their entirety.

EXAMPLES

Example 1

When the tubular medical instrument is released from the inside of a lumen of the transfer device, a shift amount between an initial position before ejection of the tubular medical instrument and a placed position after ejection is measured, and placement accuracy of the tubular medical instrument is evaluated.

As a tubular medical instrument, a self-expanding stent (hereinafter sometimes simply referred to as a stent) made from a nickel-titanium alloy and having the shape shown in FIG. 4 was prepared. In the prepared self-expanding stent, the annular sections 12 including the wavy constituent 13 were aligned in the axial direction, and at least part of the vertices 37 constituting the annular section 12 was joined to at least part of vertices constituting another adjacent annular section to constitute the connecting portion 14. Specifically, in the prepared self-expanding stent, the axial length $L_1$ was 40 mm, the maximum outer diameter $D_1$ of the central portion was 6.0 mm, the maximum outer diameter $D_2$ of one end portion was 7.0 mm, and the maximum outer diameter $D_3$ of other end portion was 7.0 mm. The one end portion and the other end portion of the self-expanding stent had a flare shape in which the outer diameter increases toward one end portion or other end portion with respect to the axial direction of the self-expanding stent.

In the weak region 16 of the stent, 15 of the annular sections 12 were aligned in the axial direction, and the number of the wavy constituents 13 constituting one of the annular sections 12 was 16, and the number of the connecting portions 14 included in one of the annular sections 12 was 4. On the other hand, in each of the strong region 15 and the strong region 17 of the stent, 2 of the annular sections 12 were aligned in the axial direction, and the number of the wavy constituents 13 constituting one of the annular sections 12 was 16, and the number of the connecting portions 14 included in one of the annular sections 12 was 16.

The number of the connecting portions 14 connecting the wavy constituent 13 constituting the annular section 12 of the weak region 16 of the stent and the wavy constituent 13 constituting the annular section 12 of the strong region 15 was 4, and the number of the connecting portions 14 connecting the wavy constituent 13 constituting the annular section 12 of the weak region 16 of the stent and the wavy constituent 13 constituting the annular section 12 of the strong region 17 of the stent was 4.

Specifically, in the weak region 16 of the stent, in the expansion state, a line connecting adjacent ones of the connecting portions 14 connected to each other without another one of the connecting portion 14 interposed between them forms two helices in directions opposite to each other with respect to the axial direction, and these helices have wavelengths different from one another.

In the weak region 16 of the stent, the central axes of the inner radii of curvature of the struts forming adjacent ones of the wavy constituents 13 were on the same straight line in the circumferential direction, and a distance between a center 31 of the inner radius of curvature of the strut of the wavy constituent 13 and a center 32 of the outer radius of curvature was 30 μm. An outer radius of curvature 34 between the struts forming the wavy constituents 13 was 110 μm and an inner radius of curvature 33 was 30 μm. A width 36 of a vertex forming the wavy constituent 13 was 110 μm, a width 35 of the strut was 80 μm, and a thickness of the strut was 200 μm.

In the strong region 15 and the strong region 17 of the stent, the central axes of the inner radii of curvature of the struts forming adjacent ones of the wavy constituents 13 were on the same straight line in the circumferential direction, and a distance between the center 31 of the inner radius of curvature of the strut of the wavy constituent 13 and the center 32 of the outer radius of curvature was 30 μm. The outer radius of curvature 34 between the struts forming the wavy constituents 13 was 115 μm and the inner radius of curvature 33 was 25 μm. The width 36 of a vertex forming the wavy constituent 13 was 120 μm, the width 35 of the strut was 90 and the thickness of the strut was 210 μm.

The nickel-titanium alloy was an alloy that exhibits a two-step phase transformation in accordance with ASTM F2063-05, and transformed into a martensitic phase, an R-phase, and an austenitic phase depending on temperature and/or stress. The tube of the nickel-titanium alloy was laser cut into the shape shown in FIG. 4 and heat treated.

For the alloy in the one end portion and in the other end portion of the self-expanding stent, heat treatment was performed 4 times in a furnace at 485° C. or more and 495° C. or less for a total of about 15 to 20 minutes, cooling was performed to room temperature under air atmosphere at an average cooling rate of 50° C./min to perform shape memory processing, and finally electropolishing was performed. For the alloy in the central portion of the self-expanding stent, heat treatment was performed 1 time in a furnace at 450° C. or more and less than 480° C. for a total of about 7 minutes, the alloy was put into cooling water so as to be rapidly cooled to perform shape memory processing, and finally electropolishing was performed.

A phase transformation temperature of the obtained stent was measured according to ASTM F2004-05 and ASTM F2005-05 using a differential scanning calorimeter ("DSC 7020" manufactured by Hitachi High-Tech Science). Measurement was performed by setting a sample mass of the stent used for measurement to 20 to 30 mg, a scanning temperature rate (that is, both a temperature lowering rate and a temperature rising rate) to 10° C./min, and a scanning temperature range (overall range at the time the temperature is lowered and at the time the temperature rises) to −120° C. to 100° C. The results of measuring the alloy in the one end portion and in the other end portion of the self-expanding stent were shown in FIG. 10 and Table 1. The results of measuring the alloy in the central portion of the self-expanding stent were shown in FIG. 11 and Table 1.

In Table 1 below, $R_s$ showed the transformation start temperature from the austenitic phase to the R-phase at cooling, $R_f$ showed the transformation finish temperature from the austenitic phase to the R-phase at cooling, $R_p$ showed the transformation peak temperature (exothermic peak temperature) from the austenitic phase to the R-phase at cooling, $M_s$ showed the transformation start temperature from the R-phase to the martensitic phase at cooling, $M_f$ showed the transformation finish temperature from the R-phase to the martensitic phase at cooling, $M_p$ showed the transformation peak temperature (exothermic peak temperature) from the R-phase to the martensitic phase at cooling, $R_s'$ showed the transformation start temperature from the martensitic phase to the R-phase at heating, $R_f'$ showed the transformation finish temperature from the martensitic phase to the R-phase at heating, $R_p'$ showed the transformation peak temperature (endothermic peak temperature) from the martensitic phase to the R-phase at heating, $A_s$ showed the transformation start temperature from the R-phase to the austenitic phase at heating, $A_f$ showed the transformation finish temperature from the R-phase to the austenitic phase at heating, and $A_p$ showed the transformation peak temperature (endothermic peak temperature) from the R-phase to the austenitic phase at heating.

Next, for the obtained self-expanding stent, the expansion force per unit length in the radial direction of the stent was calculated by a procedure described below for a region (one end portion) that includes one axial end of the stent and had a length of 10% with respect to the axial length $L_1$ of the stent, a region (other end portion) that included the other axial end of the stent and had a length of 10% with respect to the axial length $L_1$ of the stent, and a region (central portion) that included the axial center of the stent and had a length of 10% with respect to the axial length $L_1$ of the stent. A radial force measuring machine ("TTR2" manufactured by Blockwise) was used to measure the expansion force.

First, the stent in each region was compressed to reduce diameter from the radial direction at a velocity of 0.1 mm/sec from the maximum outer diameter $D_1$ (6.0 mm) of the central portion to 1.56 mm in an atmosphere of 37.0° C.±2.0° C., and a diameter reduction load a at this time was measured. Next, the contraction was relaxed in the radial direction at a rate of 0.1 mm/sec from 1.56 mm to the maximum outer diameter $D_1$ (6.0 mm), and a diameter reduction load b at this time was measured. A diameter reduction load c at the time of diameter reduction from the diameter expansion state in a diameter of a value (that is, 3.5 mm) obtained by subtracting 2.5 mm from the maximum outer diameter $D_1$ (6.0 mm) was obtained, and the diameter reduction load c was divided by a length of the one end portion, the central portion, and the other end portion of the stent to calculate an expansion force at the time of diameter reduction from the diameter expansion state. As a result of the calculation, the expansion force per unit length of the one end portion of the stent at the time of diameter reduction from the diameter expansion state was 1.121 N/mm, the expansion force per unit length of the central portion of the stent at the time of diameter reduction from the diameter expansion state was 0.979 N/mm, and the expansion force per unit length of the other end portion of the stent at the time of diameter reduction from the diameter expansion state was 1.121 N/mm.

Next, for the entire stent, the expansion force per unit length in the radial direction of the stent at the time of diameter reduction from the diameter expansion state was calculated by the same procedure as described above. That is, for measurement of the expansion force, a radial force measuring machine was used, and in the same procedure as above, the diameter reduction load c at the time of diameter reduction from the diameter expansion state in a diameter of a value (that is, 3.5 mm) obtained by subtracting 2.5 mm from the maximum outer diameter $D_1$ (6.0 mm) was obtained, and the diameter reduction load c was divided by a reference length $L_1$ (40 mm) of the stent to calculate an expansion force at the time of diameter reduction from the diameter expansion state. As a result of calculation, the expansion force per unit length of the entire stent at the time of diameter reduction from the diameter expansion state was 1.009 N/mm. Further, the transition of the expansion force with respect to the outer diameter of the stent was shown by a solid line in FIG. 12.

Next, the obtained self-expanding stent 11 was loaded into the outer shaft 72 of the transfer device for a tubular medical instrument as shown in FIG. 8 using a tubular medical instrument contraction device ("RFL225" manufactured by Blockwise). As the outer shaft 72, a tube having a braided structure, in which a polyamide elastomer was used for an outer layer, polytetrafluoroethylene (PTFE) was used for an inner layer, and a flat wire of stainless steel with a width of 100 μm and a thickness of 25 μm was used as a reinforcing layer, was used.

As shown in FIG. 8, the pusher member 74 and the inner shaft 73 were inserted into the lumen of the outer shaft 72 loaded with the self-expanding stent 11. The front end tip 75 was mounted on the distal end of the inner shaft 73 from the operator, and the operation member 76 and other members were appropriately attached to the proximal end of the inner shaft 73. Further, as shown in FIG. 9, the anti jumping layer 81 made from a polyamide elastomer having a Shore D hardness of 55 was provided as a tubular member between the self-expanding stent 11 and the inner shaft 73 and on an inner side of the other end portion of the self-expanding stent 11 to manufacture the transfer device for a tubular medical instrument 71.

The anti jumping layer 81 extends over the entire length of a unit (the strong region 17) disposed adjacent to the pusher member 74 of the self-expanding stent 11 reduced in diameter and stored in the lumen of the outer shaft 72.

The inner diameter of the outer shaft 72 was 1.56 mm, the inner diameter of the self-expanding stent 11 reduced in diameter and loaded into the lumen of the outer shaft 72 was 1.16 mm, and the outer diameter of the anti jumping layer 81 was 0.92 mm.

Next, the tubular medical instrument loaded into a lumen of the transfer device was released from the lumen, a shift amount between an initial position before ejection of the tubular medical instrument and a placed position after ejection was measured, and placement accuracy was evaluated. A device shown in FIG. 13 was preferably used for the measurement. That is, using an electric actuator ("RCS2" manufactured by TAI) appropriately connected to a power supply, a controller, and a teaching tool, the outer shaft 72 of the transfer device for a tubular medical instrument 71 was preferably held by a front chuck 121, and the outer shaft 72 was preferably pulled by a rear chuck 122 in a direction indicated by a white arrow. A tension rate was preferably, for example, 200 mm/min. The transfer device for a tubular medical instrument 71 was preferably loaded into a simulated body lumen model 124 immersed in a warm bath 123 at 37.0° C.±2.0° C. The internal diameter of the simulated body lumen model 124 was 5.0 mm, and the self-expanding stent 11 was preferably released from the transfer device into the simulated body lumen model 124. At this time, in the initial state before the release of the self-expanding stent 11, positions of one end and the other end of the self-expanding stent 11 were preferably marked on the simulated body lumen model 124 before the self-expanding stent 11 was released. When a position of the self-expanding stent 11 released and placed was marked on the simulated body lumen model 124 and a shift amount from the initial state was measured, the shift amount was considered to be small, since the expansion force at both end portions and the central portion of the self-expanding stent was appropriately adjusted.

Comparative Example 1

A self-expanding stent was manufactured under the same conditions as in Example 1, except that the conditions of heat treatment performed after laser cutting were changed.

The heat treatment, which was considered to be common to the one end portion, the central portion, and the other end portion of the self-expanding stent, was performed four times in a furnace at 485° C. or more and 495° C. or less for a total of about 15 to 20 minutes, cooling was performed to room temperature under air atmosphere at an average cooling rate of 50° C./min to perform shape memory processing, and finally electropolishing was performed to manufacture the self-expanding stent. A phase transformation temperature of the obtained stent was measured under the same conditions as in Example 1 above. Results are shown in FIG. 10 and Table 1.

Next, with respect to the obtained self-expanding stent, under the same conditions as in Example 1, the expansion force per unit length at the time of diameter reduction from the diameter expansion state of the one end portion, the central portion, and the other end portion was calculated. As a result of the calculation, the expansion force per unit length of the one end portion of the stent at the time of diameter reduction from the diameter expansion state was 1.123 N/mm, the expansion force per unit length of the central portion of the stent at the time of diameter reduction from the diameter expansion state was 0.921 N/mm, and the expansion force per unit length of the other end portion of the stent at the time of diameter reduction from the diameter expansion state was 1.128 N/mm.

Next, for the entire stent, the expansion force per unit length in the radial direction of the stent at the time of diameter reduction from the diameter expansion state was calculated under the same conditions as Example 1. As a result of calculation, the expansion force per unit length of the entire stent at the time of diameter reduction from the diameter expansion state was 1.001 N/mm. Further, the transition of the expansion force with respect to the outer diameter of the stent was shown by an alternate long and short dash line in FIG. 12.

Next, after loading the obtained self-expanding stent 11 into the outer shaft 72 of the transfer device for a tubular medical instrument under the same conditions as Example 1, the tubular medical instrument loaded in the lumen of the transfer device was released from the lumen under the same conditions as Example 1, and a shift amount between the initial position before ejection of the tubular medical instrument and a placed position after ejection was measured. As a result, the shift amount was considered to be larger than that of Example 1, because the expansion force was not appropriately adjusted by distinguishing both end portions and the central portion of the self-expanding stent.

Comparative Example 2

A self-expanding stent was manufactured under the same conditions as in Example 1, except that the conditions of heat treatment performed after laser cutting were changed. The heat treatment, which was considered to be common to the one end portion, the central portion, and the other end portion of the self-expanding stent, was performed one time in a furnace at 450° C. or more and less than 480° C. for a total of about 7 minutes, the stent was put into cooling water so as to be rapidly cooled to perform shape memory processing, and finally electropolishing was performed to manufacture the self-expanding stent. A phase transformation temperature of the obtained stent was measured under the same conditions as in Example 1 above. Results were shown in FIG. 11 and Table 1.

Next, with respect to the obtained self-expanding stent, under the same conditions as in Example 1, the expansion force per unit length at the time of diameter reduction from the diameter expansion state of the one end portion, the central portion, and the other end portion was calculated. As a result of the calculation, the expansion force per unit length of the one end portion of the stent at the time of diameter reduction from the diameter expansion state was 1.116 N/mm, the expansion force per unit length of the central portion of the stent at the time of diameter reduction from the diameter expansion state was 0.927 N/mm, and the expansion force per unit length of the other end portion of the stent was 1.110 N/mm.

Next, for the entire stent, the expansion force per unit length in the radial direction of the stent at the time of diameter reduction from the diameter expansion state was calculated under the same conditions as Example 1. As a result of calculation, the expansion force per unit length of the entire stent at the time of diameter reduction from the diameter expansion state was 1.009 N/mm. Further, the transition of the expansion force with respect to the outer diameter of the stent is shown by a dotted line in FIG. 12.

Next, after loading the obtained self-expanding stent 11 into the outer shaft 72 of the transfer device for a tubular medical instrument under the same conditions as Example 1, the tubular medical instrument loaded in the lumen of the transfer device was released from the lumen under the same conditions as Example 1, and a shift amount between the initial position before ejection of the tubular medical instrument and a placed position after ejection was measured. As a result, the shift amount was considered to be larger than that of Example 1, because the expansion force was not appropriately adjusted by distinguishing both end portions and the central portion of the self-expanding stent.

TABLE 1

| | Phase transformation temperature (° C.) | | | |
|---|---|---|---|---|
| | Example 1 | | Comparative | Comparative |
| | End portion | Central portion | example 1 | example 2 |
| $R_s$ | 25.9 | 28.4 | 25.9 | 28.4 |
| $R_p$ | 18.4 | 22.3 | 18.4 | 22.3 |
| $R_f$ | 13.3 | 17.3 | 13.3 | 17.3 |
| $M_s$ | −34.3 | −52.3 | −34.3 | −52.3 |
| $M_p$ | −56.9 | −80.5 | −56.9 | −80.5 |
| $M_f$ | −85.5 | −101.2 | −85.5 | −101.2 |
| $R_s'$ | 1.9 | −0.3 | 1.9 | −0.3 |
| $R_p'$ | 15.3 | 10.3 | 15.3 | 10.3 |
| $R_f'$ | 24.2 | 18.4 | 24.2 | 18.4 |
| $A_s$ | 18.1 | 22.0 | 18.1 | 22.0 |
| $A_p$ | 22.3 | 26.2 | 22.3 | 26.2 |
| $A_f$ | 29.3 | 31.7 | 29.3 | 31.7 |
| $A_f - R_f'$ | 5.1 | 13.3 | 5.1 | 13.3 |
| $A_p - R_p'$ | 7.0 | 15.9 | 7.0 | 15.9 |

It can be considered from Table 1 as described below. As to the phase transformation temperature of the alloy in the one end portion or the other end portion of the self-expanding stent used in Example 1, the austenitic phase transformation finish temperature $A_f$ was 29.3° C., and the difference X ($A_f - R_f'$) between the R'-phase transformation finish temperature $R_f'$ (24.2° C.) and the austenitic phase transformation finish temperature $A_f$ (29.3° C.) was 5.1° C. Further, the difference Z ($A_p - R_p'$) between the R'-phase transformation peak temperature $R_p'$ (15.3° C.) and the austenitic phase transformation peak temperature $A_p$ (22.3° C.) of the alloy in the one end portion or the other end portion of the self-expanding stent was 7.0° C. Further, at the time of heating, two endothermic peaks partially overlap each other, and the R'-phase transformation finish temperature $R_f'$ (24.2° C.) was 6.1° C. higher than the austenitic phase transformation start temperature $A_s$ (18.1° C.). Further, as to the phase transformation temperature of the alloy in the central portion of the self-expanding stent used in Example 1, the austenitic phase transformation finish temperature $A_f$ was 31.7° C., and the difference Y ($A_f - R_f'$) between the R'-phase transformation finish temperature $R_f'$ (18.4° C.) and the austenitic phase transformation finish temperature $A_f$ (31.7° C.) was 13.3° C. Further, the difference Z ($A_p - R_p'$) between the R'-phase transformation peak temperature $R_p'$ (10.3° C.) and the austenitic phase transformation peak temperature $A_p$ (26.2° C.) was 15.9° C. Further, at the time of heating, two endothermic peaks partially overlap each other, and the R'-phase transformation finish temperature $R_f'$ (18.4° C.) was 3.6° C. higher than the austenitic phase transformation start temperature $A_s$ (22.0° C.). Therefore, the difference Y ($A_f$-$R_f'$) was larger than the difference X ($A_f$-$R_f'$).

In contrast, as to the self-expanding stent used in Comparative example 1, the phase transformation temperatures of the alloy in the one end portion, the central portion, and the other end portion were the same, and the austenitic phase transformation finish temperature $A_f$ was 29.3° C., and the differences X and Y ($A_f$-$R_f'$) between the R'-phase transformation finish temperature $R_f'$ (24.2° C.) and the austenitic phase transformation finish temperature $A_f$ (29.3° C.) were 5.1° C. Therefore, the difference Y ($A_f$-$R_f'$) was equal to the difference X ($A_f$-$R_f'$). Further, the difference Z ($A_p$-$R_p'$) between the R'-phase transformation peak temperature $R_p'$ (15.3° C.) and the austenitic phase transformation peak temperature $A_p$ (22.3° C.) of the alloy in the one end portion or the other end portion of the self-expanding stent was 7.0° C. Further, at the time of heating, two endothermic peaks partially overlap each other, and, in the alloy in the one end portion or the other end portion of the self-expanding stent, the R'-phase transformation finish temperature $R_f'$ (24.2° C.) was 6.1° C. higher than the austenitic phase transformation start temperature $A_s$ (18.1° C.).

As to the self-expanding stent used in Comparative example 2, the phase transformation temperatures of the alloy in the one end portion, the central portion, and the other end portion were the same, and the austenitic phase transformation finish temperature $A_f$ was 31.7° C., and the differences X and Y ($A_f$-$R_f'$) between the R'-phase transformation finish temperature $R_f'$ (18.4° C.) and the austenitic phase transformation finish temperature $A_f$ (31.7° C.) were 13.3° C. Therefore, the difference Y ($A_f$-$R_f'$) was equal to the difference X ($A_f$-$R_f'$). Further, the difference Z ($A_p$-$R_p'$) between the R'-phase transformation peak temperature $R_p'$ (10.3° C.) and the austenitic phase transformation peak temperature $A_p$ (26.2° C.) of the alloy in the one end portion or the other end portion of the self-expanding stent was 15.9° C. Further, at the time of heating, two endothermic peaks were separated, and, in the alloy in the one end portion or the other end portion of the self-expanding stent, the R'-phase transformation finish temperature $R_f'$ (18.4° C.) was 3.6° C. lower than the austenitic phase transformation start temperature $A_s$ (22.0° C.).

Next, each of the self-expanding stent used in Example 1 and the self-expanding stents used in Comparative examples 1 and 2 will be considered based on the measurement results of the expansion force. Comparing the self-expanding stent used in Example 1 with the self-expanding stents used in Comparative examples 1 and 2, the austenitic phase transformation finish temperature $A_f$ and the expansion force had substantially equivalent values. That is, in any of the alloys constituting the self-expanding stent, the austenitic phase transformation finish temperature $A_f$ was the body temperature or less, and the expansion force per unit length in the radial direction at the one end portion and the other end portion were larger than the expansion force per unit length in the radial direction in the central portion.

Next, consideration will be made based on FIG. 12. As was clear from FIG. 12, there was no big difference between Example 1, Comparative example 1, and Comparative example 2 in the transition of the expansion force per unit length in the radial direction of the stent at the time of diameter reduction from the diameter expansion state in the entire stent. On the other hand, the transition of the expansion force per unit length in the radial direction of the stent at the time of diameter expansion from the diameter reduction state in the entire stent became larger as a whole in the order of Comparative example 1, Example 1, and Comparative example 2. Therefore, in Example 1, there was an excellent balance between the expansion force per unit length in the radial direction of the stent at the time of diameter reduction from the diameter expansion state of the entire stent and the expansion force per unit length in the radial direction of the stent at the time of diameter expansion from the diameter reduction state in the entire stent.

From the above results, the expansion force per unit length in the radial direction in the one end portion and the other end portion was made larger than the expansion force per unit length in the radial direction in the central portion, and, for the alloy constituting the one end portion or the other end portion of the self-expanding stent, the austenitic phase transformation finish temperature $A_f$ was controlled to be the body temperature or less and the difference X ($A_f$-$R_f'$) between the R'-phase transformation finish temperature $R_f'$ and the austenitic phase transformation finish temperature $A_f$ was controlled to be 1° C. or more and 12° C. or less, and, for the alloy constituting the central portion of the self-expanding stent, the austenitic phase transformation finish temperature $A_f$ was controlled to be the body temperature or less and the difference Y ($A_f$-$R_f'$) between the R'-phase transformation finish temperature $R_f'$ and the austenitic phase transformation finish temperature $A_f$ was controlled to be larger than the difference X ($A_f$-$R_f'$). In this manner, the tubular medical instrument released from the inside of a lumen of the transfer device for a tubular medical instrument can be accurately placed at an affected area.

Example 2

A ratio (difference V/difference W) calculated by a test method described below was obtained for the self-expanding stent obtained in Example 1.

(Test Method)

For one end portion and another end portion of the stent, in a case the average diameter in an expanded state at the one end portion and the other end portion of the stent was defined as 100%, the diameter was reduced such that the average diameter becomes 25%. The average diameter at the one end portion and the other end portion was 6 mm, the width of the strut was 90 μm, and the average diameter reduction rate was 0.1 mm/sec. At the time of the diameter reduction, the expansion force per unit length in the radial direction at the one end portion or the other end portion when the average diameter became 75% was obtained. Next, for a central portion of the stent, in a case the average diameter at the central portion of the stent was 100%, the diameter was reduced such that the average diameter becomes 25%. At the time of the diameter reduction, the expansion force per unit length in the radial direction in the central portion when the average diameter became 75% was obtained. The average diameter in the central portion was 6 mm and the width of the strut was 80 μm. The difference V was calculated by subtracting the expansion force per unit length in the radial direction in the central portion from the smaller one of the expansion force per unit length in the radial direction in the one end portion or the other end portion. In a case the diameter was expanded such that the average diameter became 100% after diameter reduction, the difference W was calculated by subtracting the expansion force per unit length in the radial direction in the central portion from the smaller one of the expansion force per unit length in the radial direction in the one end portion and the other end portion when the average diameter of the stent became 75%. The average diameter expansion rate was 0.1 mm/sec. Next, the ratio (difference V/difference W) between the difference V and the difference W was calculated.

The relationship between the outer diameter of the stent and the expansion force at the end portion and in the central portion of the stent was shown in FIG. 14. In FIG. 14, the solid line indicates the measurement result at the end portion of the stent, and the alternate long and short dash line indicates the measurement result in the central portion of the stent. Note that, since the results of the one end portion and the other end portion of the stent were the same, FIG. 14 showed them simply as the end portion. A result of calculating the ratio (difference V/difference W) was 4.8.

Comparative Example 3

Using a self-expanding stent (trade name: EPIC) manufactured by Boston Scientific, the ratio (difference V/difference W) was obtained in the same procedure as in Example 2. Note that the average diameter in one end portion and another end portion was 8 mm, and the average diameter in a central portion was 8 mm.

The relationship between the outer diameter of the stent and the expansion force at the end portion and in the central portion of the stent was shown in FIG. 15. In FIG. 15, the solid line indicates the measurement result at the end portion of the stent, and the alternate long and short dash line indicates the measurement result in the central portion of the stent. Note that, since the results of the one end portion and the other end portion of the stent were the same, FIG. 15 showed them simply as the end portion. A result of calculating the ratio (difference V/difference W) was 1.7.

Comparative Example 4

Using a self-expanding stent (trade name: SMART) manufactured by Cardinal Health, Inc. (Cordis), the ratio (difference V/difference W) was obtained in the same procedure as in Example 2. Note that the average diameter in one end portion and another end portion was 8 mm, and the average diameter in a central portion was 8 mm.

The relationship between the outer diameter of the stent and the expansion force at the end portion and in the central portion of the stent was shown in FIG. 16. In FIG. 16, the solid line indicates the measurement result at the end portion of the stent, and the alternate long and short dash line indicates the measurement result in the central portion of the stent. Note that, since the results of the one end portion and the other end portion of the stent were the same, FIG. 16 showed them simply as the end portion. A result of calculating the ratio (difference V/difference W) was −4.3.

Comparative Example 5

A self-expanding stent was manufactured under the same conditions as in Comparative example 1, except that the stent design was changed. That is, as the tubular medical instrument, a self-expanding stent made from a nickel-titanium alloy and having an entire shape including only the weak region 16 as shown in FIG. 4 was prepared. Specifically, in the prepared self-expanding stent, the axial length $L_1$ was 40 mm, the maximum outer diameter $D_1$ of the central portion was 8.0 mm, the maximum outer diameter $D_2$ of the one end is 9.0 mm, and the maximum outer diameter $D_3$ of the other end portion was 9.0 mm. The one end portion and the other end portion of the self-expanding stent had a flare shape in which the outer diameter increases toward one end portion or another end portion with respect to the axial direction of the stent.

In the self-expanding stent, the annular sections 12 including the wavy constituent 13 were aligned in the axial direction, and at least part of the vertices 37 constituting the annular section 12 was joined to at least part of vertices constituting another adjacent annular section to constitute the connecting portion 14. In the self-expanding stent, 19 of the annular sections 12 were aligned in the axial direction, and the number of the wavy constituents 13 constituting one of the annular sections 12 was 16, and the number of the connecting portions 14 included in one of the annular sections 12 was 4. Specifically, in the self-expanding stent, in the expansion state, a line connecting adjacent ones of the connecting portions 14 connected to each other without another one of the connecting portion 14 interposed between them forms two helices in directions opposite to each other with respect to the axial direction, and these helices have wavelengths different from each other.

In the self-expanding stent, the central axes of the inner radii of curvature of the struts forming adjacent ones of the wavy constituents 13 were on the same straight line in the circumferential direction, and a distance between a center 31 of the inner radius of curvature of the strut of the wavy constituent 13 and a center 32 of the outer radius of curvature was 40 µm. The outer radius of curvature 34 between the struts forming the wavy constituents 13 was 120 µm and the inner radius of curvature 33 was 30 µm. The width 36 of a vertex forming the wavy constituent 13 was 130 µm, the width 35 of the strut was 100 µm, and a thickness of the strut was 200 µm.

Using the self-expanding stent, the ratio (difference V/difference W) was obtained in the same procedure as in Example 2. Note that the average diameter in one end portion and another end portion was 8 mm, and the average diameter in a central portion was 8 mm.

The relationship between the outer diameter of the stent and the expansion force at the end portion and in the central portion of the stent was shown in FIG. 17. In FIG. 17, the solid line indicates the measurement result at the end portion of the stent, and the alternate long and short dash line indicates the measurement result in the central portion of the stent. Note that, since the results of the one end portion and the other end portion of the stent were the same, FIG. 17 showed them simply as the end portion. A result of calculating the ratio (difference V/difference W) was 1.1.

As was clear from the results of Example 2 and Example 1, the tubular medical instrument defined in the present invention appropriately adjusts the expansion force in the radial direction in both end portions and the central portion in the axial direction. For this reason, it is considered that the tubular medical instrument can be easily ejected from the transfer device, and the tubular medical instrument released from the inside of the lumen of the transfer device can be accurately placed at an affected area. On the other hand, in Comparative examples 3 to 5, the expansion force in the radial direction is not appropriately adjusted in both end portions and in the central portion in the axial direction. For this reason, it is considered that the tubular medical instrument cannot be easily ejected from the transfer device, and the tubular medical instrument released from the inside of the lumen of the transfer device cannot be accurately placed at an affected area.

DESCRIPTION OF REFERENCE SIGNS

11: a self-expanding stent
12: an annular section
13: a wavy constituent
14: a connecting portion
15: a strong region
16: a weak region
17: a strong region
31: a center of the inner radius of curvature
32: a center of the outer radius of curvature
33: an inner radius of curvature
34: an outer radius of curvature
35: a width of the strut
36: a width of a vertex
37: a vertice
71: a transfer device for a tubular medical instrument
72: an outer shaft
73: an inner shaft
74: a pusher member
75: a front end tip
76: an operation member
81: an anti jumping layer
121: a front chuck
122: a rear chuck
123: a warm bath
124: a simulated body lumen model
$L_1$: an axial length
$D_1$: a maximum outer diameter (a maximum outer diameter of the central portion)
$D_2$: a maximum outer diameter (a maximum outer diameter of one end portion)
$D_3$: a maximum outer diameter (a maximum outer diameter of another end portion)
$R_s$: a R-phase transformation start temperature
$R_p$: a R-phase transformation peak temperature
$R_f$: a R-phase transformation finish temperature
$M_s$: a martensitic phase transformation start temperature
$M_p$: a martensitic phase transformation peak temperature
$M_f$: a martensitic phase transformation finish temperature
$R_s'$: a R'-phase transformation start temperature
$R_p'$: a R'-phase transformation peak temperature
$R_f'$: a R'-phase transformation finish temperature
$A_s$: an austenitic phase transformation start temperature
$A_p$: an austenitic phase transformation peak temperature
$A_f$: an austenitic phase transformation finish temperature
T: an environmental temperature
A: an austenitic phase
R: a R-phase
M: a martensitic phase

The invention claimed is:

1. A tubular medical instrument made of an alloy, comprising:
one end portion, the other end portion, and a central portion, wherein
the one end portion is a region including one axial end of the tubular medical instrument and having a length of 10% with respect to an axial length $L_1$ of the tubular medical instrument,
the other end portion is a region including the other axial end of the tubular medical instrument and having a length of 10% with respect to the axial length $L_1$ of the tubular medical instrument,
the central portion is a region including an axial center of the tubular medical instrument and having a length of 10% with respect to the axial length $L_1$ of the tubular medical instrument,
the tubular medical instrument comprises annular sections comprising a wavy constituent, wherein the annular sections are formed to include the wavy constituent and aligned in an axial direction, opposing vertices of the wavy constituents in adjacent annular sections are arranged so as to shift from each other with respect to a circumferential direction in the central portion, and opposing vertices of the wavy constituents in adjacent annular sections are arranged without being shifted from each other in the circumferential direction in the one end portion and the other end portion, and
a ratio (difference V/difference W) calculated by the following test method is 3 or more:
the tubular medical instrument is subjected to a contraction-expansion cycle where the tubular medical instrument is contracted from an expanded state to a contracted state such that an average diameter of the tubular instrument becomes 25%, and then allowed to expand from the contracted state to the expanded state, wherein
the difference V is a difference between an expansion force per unit length in the radial direction in the central portion and an expansion force per unit length in the radial direction in the one end portion or the other end portion, whichever is smaller, at the time when the average diameter becomes 75% as the tubular medical instrument is being contracted from the expanded state such that the average diameter of the tubular instrument becomes 25%,
the difference W is a difference between an expansion force per unit length in the radial direction in the central portion and an expansion force per unit in the radial direction in the one end portion or the other end portion, whichever is smaller, at the time when the average diameter becomes 75% as the tubular medical instrument is being allowed to expanded from the contracted state, and
the expansion force per unit length in the radial direction in the one end portion and the other end portion is larger than the expansion force per unit length in the radial direction in the central portion at the time when the average diameter becomes 75%.

2. The tubular medical instrument according to claim 1, wherein
a maximum outer diameter $D_2$ of the one end portion and a maximum outer diameter $D_3$ of the other end portion are larger than a maximum outer diameter $D_1$ of the central portion.

3. The tubular medical instrument according to claim 1, wherein
the wavy constituent is expandable in the circumferential direction,
at least part of the wavy constituent constituting one of the annular sections is connected to at least part of a wavy constituent constituting another adjacent annular section at their vertices, and
a number a or a number b, whichever is smaller, is larger than a number c, where the number a is defined as a number of connecting portions between an annular section $A_1$ in the one end portion and another annular section $A_2$ adjacent to the annular section $A_1$, the number b is defined as a number of connecting portions between an annular section $B_1$ in the other end portion and another annular section $B_2$ adjacent to the annular section $B_1$, and the number c is defined as a number of connecting portions between an annular section $C_1$ in the central portion and another annular section $C_2$ adjacent to the annular section $C_1$.

4. The tubular medical instrument according to claim 1, wherein
the tubular medical instrument comprises annular sections,
a first annular section of said annular sections at one end of the tubular medical instrument is connected at all vertices to another annular section adjacent to the first annular section,
a second annular section of said annular sections at another end of the tubular medical instrument is connected at all vertices to another annular section adjacent to the second annular section, and
at least part of the third annular section of said annular sections in the central portion is connected at part of vertices to another annular section adjacent to the third annular section, and is not connected at part of vertices.

5. The tubular medical instrument according to claim 1, wherein
the alloy has the austenitic phase transformation finish temperature $A_f$ of 15° C. or more and 37° C. or less.

6. The tubular medical instrument according to claim 1, wherein
the alloy in the one end portion or the other end portion has a difference between an R'-phase transformation peak temperature $R_p'$ and an austenitic phase transformation peak temperature $A_p$ of 1° C. or more and 12° C. or less.

7. The tubular medical instrument according to claim 1, wherein
the alloy in the one end portion or the other end portion has a R'-phase transformation finish temperature $R_f'$ higher than an austenitic phase transformation start temperature $A_s$.

8. The tubular medical instrument according to claim 7, wherein
the alloy in the one end portion or the other end portion has the R'-phase transformation finish temperature $R_f'$ higher than the austenitic phase transformation start temperature $A_s$ by 1° C. or more and 10° C. or less.

9. The tubular medical instrument according to claim 1, wherein
the tubular medical instrument is a self-expanding stent.

10. A transfer device for a tubular medical instrument including the tubular medical instrument according to claim 1.

11. The transfer device for the tubular medical instrument according to claim 10, comprising
an outer shaft having a lumen,
the tubular medical instrument stored in the lumen of the outer shaft,
an inner shaft disposed in the lumen of the tubular medical instrument, and
a tubular member provided between the tubular medical instrument and the inner shaft and on an inner side of at least one of one end portion and the other end portion of the tubular medical instrument, wherein
a difference between an inner diameter of the tubular medical instrument stored in the lumen of the outer shaft and an outer diameter of the tubular member is 0.05 mm or more and 0.35 mm or less.

* * * * *